United States Patent
Aoki

(10) Patent No.: US 9,080,940 B2
(45) Date of Patent: Jul. 14, 2015

(54) SENSOR CHIP THAT IS USED IN SPECIMEN MATERIAL DETECTION DEVICE AND SPECIMEN MATERIAL DETECTION DEVICE USING SENSOR CHIP

(75) Inventor: Youichi Aoki, Tokyo (JO)

(73) Assignee: KONICA MINOLTA, INC. (JP)

( * ) Notice: Subject to any disclaimer, the term of this patent is extended or adjusted under 35 U.S.C. 154(b) by 0 days.

(21) Appl. No.: 14/125,899

(22) PCT Filed: May 31, 2012

(86) PCT No.: PCT/JP2012/064147
§ 371 (c)(1),
(2), (4) Date: Dec. 12, 2013

(87) PCT Pub. No.: WO2012/172992
PCT Pub. Date: Dec. 20, 2012

(65) Prior Publication Data
US 2014/0118747 A1    May 1, 2014

(30) Foreign Application Priority Data

Jun. 14, 2011    (JP) ................... 2011-132103

(51) Int. Cl.
G01N 21/55    (2014.01)
G01N 21/05    (2006.01)
G01N 21/552    (2014.01)
G01N 21/64    (2006.01)
G01N 21/03    (2006.01)

(52) U.S. Cl.
CPC ............... *G01N 21/05* (2013.01); *G01N 21/55* (2013.01); *G01N 21/553* (2013.01); *G01N 21/64* (2013.01); *G01N 21/648* (2013.01); *G01N 2021/0325* (2013.01); *G01N 2021/0346* (2013.01)

(58) Field of Classification Search
CPC ... G01N 21/553; G01N 21/55; G01N 21/554; G01N 21/474; G01N 21/57
USPC .......................................... 356/445
See application file for complete search history.

(56) References Cited

U.S. PATENT DOCUMENTS

| 5,637,469 A | 6/1997 | Wilding et al. |
| 7,715,012 B2* | 5/2010 | Ogura et al. .................. 356/445 |

(Continued)

FOREIGN PATENT DOCUMENTS

| JP | 2005069997 A | 3/2005 |
| JP | 2006090985 A | 4/2006 |
| JP | 2007093266 A | 4/2007 |

(Continued)

OTHER PUBLICATIONS

Extended European Search Report for Application No./Patent No. 12801279.6-1554/2722663, issued Oct. 21, 2014.

(Continued)

*Primary Examiner* — Tarifur Chowdhury
*Assistant Examiner* — MD Rahman
(74) *Attorney, Agent, or Firm* — Cantor Colburn LLP

(57) ABSTRACT

A sensor chip maybe provided that is used in a specimen material detection device with which a solution can be prevented from remaining, an irregularity can be prevented from occurring in a concentration, and a fluctuation of a signal can be prevented from occurring during a detection, and as a result it is possible to carry out an inspection in an accurate manner.

10 Claims, 27 Drawing Sheets

(56) References Cited

U.S. PATENT DOCUMENTS 8,705,039 B2 * 4/2014 Cho et al. .................. 356/445
2006/0197954 A1 * 9/2006 Ogura et al. ............... 356/445

FOREIGN PATENT DOCUMENTS

| | | |
|---|---|---|
| JP | 2007322284 A | 12/2007 |
| WO | 2009145172 A1 | 12/2009 |
| WO | 2011027851 A1 | 3/2011 |

OTHER PUBLICATIONS

Written Opinion of the International Searching Authority for International Application No. PCT/JP2012/064147, mailed Aug. 28, 2012, with English translation.

International Search Report for International Application No. PCT/JP2012/064147; Date of Mailing: Aug. 28, 2012.

* cited by examiner

Relationship among the dimension of a flow passage, the maximum Reynolds number, a laminar flow region, and a turbulent flow region

SENSOR CHIP THAT IS USED IN SPECIMEN MATERIAL DETECTION DEVICE AND SPECIMEN MATERIAL DETECTION DEVICE USING SENSOR CHIP

CROSS REFERENCE TO RELATED APPLICATIONS

This is the U.S. national stage of application No. PCT/JP2012/064147, filed on 31 May 2012. Priority under 35 U.S.C. §119(a) and 35 U.S.C. §365(b) is claimed from Japanese Application No. 2011-132103, filed 14 Jun. 2011, the disclosure of which is also incorporated herein by reference.

TECHNICAL FIELD

The present invention relates to a sensor chip that is used in a specimen material detection device and a specimen material detection device using a sensor chip for a surface plasmon resonance device (hereafter referred to as an SPR device) using a phenomenon of a surface plasmon resonance (SPR: Surface Plasmon Resonance) and a surface plasmon-field enhanced fluorescence spectroscopy measurement device (hereafter referred to as an SPFS device) using a principle of a surface plasmon excitation enhanced fluorescence spectroscopy (SPFS: Surface Plasmon-field enhanced Fluorescence Spectroscopy) for the fields of a medical care and biotechnology for instance.

BACKGROUND ART

In the case in which a detection of an extremely fine substance is carried out, a wide variety of specimen material detection device has been used for enabling an inspection of such a substance by putting a physical phenomenon of a substance to practical use from the past.

As one of such specimen material detection devices, there can be mentioned for instance an SPR device in which a phenomenon for obtaining a high optical output by a resonance of an electron and a light in a minute region of a nanometer level or the like (a surface plasmon resonance (SPR: Surface Plasmon Resonance) phenomenon) is put to practical use and an extremely fine analyte in a biological body is detected for instance.

As one of such specimen material detection devices, there also can be mentioned for instance an SPFS device in which the analyte detection can be carried out with a higher degree of accuracy as compared with the SPR device based on a principle of a surface plasmon excitation enhanced fluorescence spectroscopy (SPFS) for putting a surface plasmon resonance phenomenon to practical use.

For the surface plasmon excitation enhanced fluorescence spectroscopy (SPFS), under the condition of the attenuated total reflectance (ATR) of an excitation light such as a laser light that has been applied from the light source on a surface of a metallic thin film, by generating a surface plasmon light (a crude density wave) on a surface of a metallic thin film, a photon amount that is included in an excitation light that has been applied from the light source is increased by several ten times to several hundred times to obtain an electric field enhancement effect of a surface plasmon light.

By the electric field enhancement effect, a fluorescence substance that has been coupled (labeled) with an analyte that has been captured near a surface of a metallic thin film is excited in an efficient manner. By observing the fluorescence, an analyte of an infinitesimal quantity and/or an extremely low concentration is detected in the above method.

For such a specimen material detection device such as an SPR device and an SPFS device, a specimen material solution that contains an analyte (antigen) that is a detection target is prepared in advance, the specimen material solution is sent to a fine flow passage, and an analyte (antigen) is captured with a ligand (antibody) that is fixed to a detection region (a reaction field) that is disposed in the fine flow passage.

For such a specimen material detection device, a solution sending of a ligand solution, a specimen material solution, and a cleaning solution is carried out in a fine flow passage by ordinary.

In this case, there can be mentioned for instance a specimen material detection device that is called a circulation type in which a specimen material solution is circulated and passes through a detection region in a repetitive manner and a system that is called a reciprocation type in which a specimen material solution is reciprocated and passes through a detection region in a repetitive manner in addition to a system that is called a one pass type in which a specimen material solution passes through a detection region only one time.

For instance, the Patent Literature 1 (Japanese Patent Application Laid-Open Publication No. 2006-90985) discloses a specimen material detection device that is called a reciprocation type as described above.

More specifically, the measurement device that is disclosed in the Patent Literature 1 is provided with a first sending and discharge means such as a pipette capable of performing a discharge of an analyte solution to and the suction of an analyte solution from a flow passage. In the description of the Patent Literature 1, by sending an analyte solution to a sensor face by the discharge and then carrying out a reverse flow by a suction of the analyte solution by using the first sending and discharge means, an analyte solution is reciprocated on a sensor face at least once, and the analyte solution is sent to the sensor face again after that.

PRIOR ART DOCUMENTS

Patent Literature

[Patent Literature 1]
Japanese Patent Application Laid-Open Publication No. 2006-90985

SUMMARY OF INVENTION

Problems to be Solved by the Invention

Any one of the specimen material detection devices of a one pass type, a circulation type, and a reciprocation type as described above has the following problem.

FIG. 23 is a schematic view for showing a specimen material detection device 100 of a reciprocation type for instance.

As shown in FIG. 23, the specimen material detection device 100 is provided with a fine flow passage 102 and a solution sending pump 106 that is configured to send a solution 104 such as a ligand solution, a specimen material solution, and a cleaning solution.

As shown in FIGS. 23 and 24 moreover, the fine flow passage 102 is provided with an inflow outflow hole 108 that is an inflow outflow hole that is configured to make a solution 104 inflow to and outflow from the fine flow passage 102 on an edge part of one side in a direction of the flow passage, and an outlet hole 110 that is an outlet of a solution 104 that outflows from the inflow outflow hole 108 on an edge part of the other side in a direction of the flow passage.

A detection region (a reaction field) 112 to which an antibody (a ligand) that reacts with a specific antigen is fixed is disposed on a bottom surface in the fine flow passage 102. In the case in which a solution 104 that includes a specific antigen (analyte) is sent by a solution sending pump 106, the solution 104 passes through the detection region 112 of the fine flow passage 102 in a repetitive manner.

As shown in FIG. 23 moreover, a pipette 114 that has held the solution 104 is connected to the side of a top surface of the inflow outflow hole 108. The pipette 114 is configured so as to be used attachably to and detachably from the inflow outflow hole 108 of the fine flow passage 102.

A solution sending pump 106 is attached to the upper part of the pipette 114. The solution sending pump 106 is communicated with a control part 116. By the control of the control part 116, the solution 104 that has been held in the pipette 114 can be discharged to the fine flow passage 102, or the solution 104 that has been stored in the fine flow passage 102 and a mixing part 118 can be sucked to the pipette 114.

For the specimen material detection device 100 that is configured as described above, after a first solution 104 such as a specimen material solution is made inflow from the inflow outflow hole 108 and the first solution 104 is removed from the inflow outflow hole 108 for instance, another second solution is made inflow into a flow passage, or after a first solution 104 is made inflow into the fine flow passage 102, another second solution is made inflow into a flow passage via a driving gas such as an air. The above described cases are provided with the following problem.

In other words, as shown in FIG. 24, in the case in which a width b of the fine flow passage 102 that comes into contact with the inflow outflow hole 108 is equal to or larger than the maximum width a of the inflow outflow hole 108 (a diameter a of the inflow outflow hole 108 in this case), the following problem takes its rise.

In this case, in the case in which the first solution 104 is discharged from the inflow outflow hole 108, a flow rate is low at a wall surface of the fine flow passage 102 and a flow rate is high at the center part in a direction of a width of the first solution 104 in the fine flow passage 102 unfortunately. Consequently, as shown in FIG. 25, a solution back end 120 at the center part in a direction of a width of the first solution 104 in the fine flow passage 102 reaches the inflow outflow hole 108 at first, and the first solution 104 remains at the both ends in a direction of a width near a contact point of the inflow outflow hole 108 and the fine flow passage 102, thereby causing a residue of a solution.

In particular, in the case of a sandwich assay in which a cleaning solution, a specimen material solution, a cleaning solution, and a reaction test reagent are made inflow in this order into the fine flow passage 102, in the case in which the previous solution remains, the next test reagent is diluted. As a result, an irregularity occurs in a concentration and a fluctuation of a signal occurs during a detection, whereby the detection accuracy is deteriorated.

Consequently, for a mechanism that is configured to carry out an assay in a flow passage with a minute sample as described above, a shape of a flow passage has a deep relationship with a fluctuation of a measurement.

For such a problem, any one of the specimen material detection devices of a one pass type, a circulation type, and a reciprocation type of a conventional configuration has a similar problem.

On the other hand, for the Patent Literature 1, the maximum width (diameter) of the inflow outflow hole and a width of a flow passage are equivalent to each other, and the maximum width (diameter) of the inflow outflow hole and a width of a flow passage are not considered, whereby it is clarified that the above described problem occurs unfortunately.

The present invention was made in consideration of such a condition, and an object of the present invention is to provide a sensor chip that is used in a specimen material detection device and a specimen material detection device using a sensor chip, in which the first solution can be prevented from remaining at the both ends in a direction of a width near a contact point of the inflow outflow hole and the fine flow passage, whereby a residue of a solution can be prevented, and an irregularity can be prevented from occurring in a concentration and a fluctuation of a signal can be prevented from occurring during a detection, whereby an inspection can be carried out in a precise manner, in the case in which after a first solution such as a specimen material solution is made inflow from the inflow outflow hole and the first solution is removed from the inflow outflow hole, a second solution is made inflow into a flow passage, or after a first solution is made inflow into the flow passage, a second solution is made inflow into a flow passage via an air that is a driving gas.

Means for Solving the Problems

The present invention was made in order to solve the problems of the conventional art described above and achieve the purpose.

A sensor chip that is used in a specimen material detection device in accordance with the present invention is characterized by comprising:

a flow passage that is provided with a detection region; and an inflow outflow hole that is connected to an edge part of one side of the flow passage and that is configured to be able to make a solution inflow to and outflow from the flow passage, wherein:

after a first solution is made inflow from the inflow outflow hole and the first solution is removed from the flow passage, a second solution is made inflow into the flow passage from the inflow outflow hole, or after a first solution is made inflow into the flow passage from the inflow outflow hole, a second solution is made inflow into a flow passage from the inflow outflow hole via a driving gas, and the sensor chip is configured in such a manner that the relationship between the maximum width (a) of the inflow outflow hole and the width (b) of the flow passage is a>b, and an angle θ that is formed between a wall surface of the flow passage and the tangent line of the inflow outflow hole at a contact point of the inflow outflow hole and the flow passage is in the range of 90°≤θ≤135°.

As described above, the present invention is configured in such a manner that the relationship between the maximum width (a) of the inflow outflow hole and the width (b) of the flow passage is a>b, and an angle θ that is formed between a wall surface of the flow passage and the tangent line of the inflow outflow hole at a contact point of the inflow outflow hole and the flow passage is in the range of 90°≤θ≤135°.

By this configuration, in the case in which after a first solution such as a specimen material solution is made inflow from the inflow outflow hole and the first solution is removed from the inflow outflow hole, a second solution is made inflow into a flow passage, or after a first solution is made inflow into the flow passage, a second solution is made inflow into a flow passage via an air that is a driving gas for instance, as shown in Table 1 that will be described later, the first solution can be prevented from remaining at the both ends in a direction of a width near a contact point of the inflow outflow hole and the fine flow passage, whereby a residue of a solution can be prevented, and an irregularity can be prevented from occurring in a concentration and a fluctuation of a signal can be prevented from occurring during a detection, whereby an inspection can be carried out in a precise manner.

The sensor chip in accordance with the present invention is characterized in that:

for a system in which a distance L from an end part on a side of the flow passage of the inflow outflow hole to a center of the detection region is at least 1 mm, and a solution in which a degree of viscosity at 20° C. is in the range of 1 to 3 mPa*s is sent at an average flow rate in the range of 1 to 5000 μl/min, flow passage length L×variable A<200 (kPa), where the variable A=8×[(flow passage height h+flow passage width b)$^2$×10$^3$/{(flow passage height h×flow passage width b)$^3$×60}], and the units are μl/min for a flow rate, μm for a flow passage height, μm for a flow passage width, μm for a flow passage length, and mPa*s for a degree of viscosity.

Here, an average flow rate is calculated by a time from a start of a movement of a solution by a solution sending to a stop of a movement of a solution and an amount of a solution that has been moved. In the case in which a cross sectional area of a flow passage is constant, "an amount of a solution that has been moved" can be calculated from an amount of a movement of a solution by the image analysis. Moreover, a flow rate instrument can also be used. Furthermore, "a time from a start of a movement of a solution to a stop of a movement of a solution" can also be obtained by the image analysis for instance.

In other words, in the case in which a distance L from an end part on a side of the flow passage of the inflow outflow hole to a center of the detection region is too short for the flow passage that comes into contact with the inflow outflow hole, a flow of a solution that has just flown from the inflow outflow hole is turbulent. In addition, in the case in which a solution that is measured stagnates, a disturbance occurs for the index of refraction. Consequently, for the SPR device and the SPFS device in which the index of refraction has a huge effect on the accuracy of an inspection, the large variations have a huge effect on the accuracy of a measurement in the case in which a measurement is carried out.

Consequently, it is necessary that a location of the detection region in the flow passage is set apart by a constant distance from the inflow outflow hole and a measurement is carried out at a location in which a flow of a solution is stable.

However, even in the case in which a distance L from an end part on a side of the flow passage of the inflow outflow hole to a center of the detection region is too long, the configuration creates an adverse result.

In other words, the relationship between the maximum width (a) of the inflow outflow hole and the width (b) of the flow passage is a>b and a flow passage height is small as described above. Consequently, in the case in which a distance L is set to be long, a resistance of the flow passage becomes large. Therefore, in the case in which a resistance of the flow passage becomes large, a pressure that is applied during a solution sending becomes large. As a result, a leakage of a solution occurs from the inflow outflow hole or a junction part of the inflow outflow hole and the flow passage.

In particular, for the configuration of a solution sending that is provided with an air damper in a solution sending system, in addition to a leakage of a solution, a movement of a plunger and an amount of a solution that is sent do not keep pace with each other and a speed of a plunger and a rate of a solution sending vary more greatly in the case in which a resistance in the flow passage is larger. As a result, a desired amount of a solution cannot be sent, a sensitivity of a measurement is degraded, and a fluctuation of a measurement becomes larger.

Consequently, it is not preferable that a distance L is too long from the aspect of the performance of a solution sending and a fluctuation of a measurement. Moreover, it is also not preferable that a distance L is too short from the aspect of a fluctuation of a measurement caused by a turbulence of a solution.

As a result, like the configuration of the present invention, it is preferable that:

for a system in which a distance L from an end part on a side of the flow passage of the inflow outflow hole to a center of the detection region is at least 1 mm, and a solution in which a degree of viscosity at 20° C. is in the range of 1 to 3 mPa*s is sent at an average flow rate in the range of 1 to 5000 μl/min, flow passage length L×variable A<200 (kPa), where the variable A=8×[(flow passage height h+flow passage width b)$^2$×10$^3$/{(flow passage height h×flow passage width b)$^3$×60}], and the units are μl/min for a flow rate, μm for a flow passage height, μm for a flow passage width, μm for a flow passage length, and mPa*s for a degree of viscosity.

By this configuration, as shown in Table 2 that will be described later and FIG. 12, a solution that flows in the flow passage is in the range of a laminar flow region, a turbulent flow does not occur in the flow passage, and a laminar flow causes a uniform flow. Consequently, a stagnation of a solution does not occur in the flow passage. As a result, the detection region in the flow passage is not provided with a disturbance of the index of refraction, and a fluctuation of a signal can be prevented from occurring during a detection, whereby an inspection can be carried out in a precise manner.

The sensor chip in accordance with the present invention is characterized in that a distance L from an end part on a side of the flow passage of the inflow outflow hole to a center of the detection region is set to be in the range of 1 to 50 mm.

In the case in which a distance L from an end part on a side of the flow passage of the inflow outflow hole to a center of the detection region is set to be in the range of 1 to 50 mm as described above, a turbulent flow does not occur in the flow passage, and a laminar flow causes a uniform flow. Consequently, a stagnation of a solution does not occur in the flow passage. As a result, the detection region in the flow passage is not provided with a disturbance of the index of refraction, and a fluctuation of a signal can be prevented from occurring during a detection, whereby an inspection can be carried out in a precise manner.

The sensor chip in accordance with the present invention is characterized in that a solution that is made inflow into the flow passage is reciprocated and passes through the detection region.

For a specimen material detection device that is called a reciprocation type in which a solution that is made inflow into the flow passage is reciprocated and passes through the detection region, the first solution can be prevented from remaining at the both ends in a direction of a width near a contact point of the inflow outflow hole and the fine flow passage, whereby a residue of a solution can be prevented, as shown in Table 1 that will be described later, and an irregularity can be prevented from occurring in a concentration and a fluctuation of a signal can be prevented from occurring during a detection, whereby an inspection can be carried out in a precise manner.

The sensor chip in accordance with the present invention is characterized in that:

a second inflow outflow hole is connected to the other end side of the flow passage, the relationship between the maximum width (a) of the second inflow outflow hole and the width (b) of the flow passage is a>b, and an angle θ that is formed between a wall surface of the flow passage and the tangent line of the second inflow outflow hole at a contact point of the second inflow outflow hole and the flow passage is in the range of 90°≤θ≤135°.

By this configuration, the first solution can be prevented from remaining at the both ends in a direction of a width near a contact point of the second inflow outflow hole and the fine flow passage, whereby a residue of a solution can be prevented, as shown in Table 1 that will be described later, and an irregularity can be prevented from occurring in a concentration and a fluctuation of a signal can be prevented from occurring during a detection, whereby an inspection can be carried out in a precise manner.

The sensor chip in accordance with the present invention is characterized in that:

for a system in which a distance L from an end part on a side of the flow passage of the second inflow outflow hole to a center of the detection region is at least 1 mm for the second inflow outflow hole, and a solution in which a degree of viscosity at 20° C. is in the range of 1 to 3 mPa*s is sent at an average flow rate in the range of 1 to 5000 μl/min, flow passage length L×variable A<200 (kPa), where the variable A=8×[(flow passage height h+flow passage width b)$^2$×10$^3$/{(flow passage height h×flow passage width b)$^3$×60}], and the units are μl/min for a flow rate, μm for a flow passage height, μm for a flow passage width, μm for a flow passage length, and mPa*s for a degree of viscosity.

By this configuration, a solution that flows in the flow passage is in the range of a laminar flow region, a turbulent flow does not occur in the flow passage, and a laminar flow causes a uniform flow. Consequently, a stagnation of a solution does not occur in the flow passage. As a result, the detection region in the flow passage is not provided with a disturbance of the index of refraction, and a fluctuation of a signal can be prevented from occurring during a detection, whereby an inspection can be carried out in a precise manner.

The sensor chip in accordance with the present invention is characterized in that a distance L from an end part on a side of the flow passage of the second inflow outflow hole to a center of the detection region is set to be in the range of 1 to 50 mm.

In the case in which a distance L from an end part on a side of the flow passage of the second inflow outflow hole to a center of the detection region is set to be in the range of 1 to 50 mm as described above, a turbulent flow does not occur in the flow passage, and a laminar flow causes a uniform flow. Consequently, a stagnation of a solution does not occur in the flow passage. As a result, the detection region in the flow passage is not provided with a disturbance of the index of refraction, and a fluctuation of a signal can be prevented from occurring during a detection, whereby an inspection can be carried out in a precise manner.

The sensor chip in accordance with the present invention is characterized by further comprising a mixing part at the second inflow outflow hole in such a manner that the mixing part is configured to store a solution that has passed through the detection region of the flow passage on a temporary basis and to stir the solution that has been stored.

For any one of the specimen material detection devices of a circulation type and a reciprocation type in which a specimen material solution passes through a reaction field of the fine flow passage in a repetitive manner, in the case in which the specimen material detection device is provided with a mixing part, a reaction efficiency can be prevented from being degraded, and a solution can be sent in a repetitive manner.

A specimen material detection device in accordance with the present invention is characterized by comprising a sensor chip as defined in any one of the above descriptions.

By this configuration, the first solution can be prevented from remaining at the both ends in a direction of a width near a contact point of the inflow outflow hole and the fine flow passage, whereby a residue of a solution can be prevented, as shown in Table 1 that will be described later, and an irregularity can be prevented from occurring in a concentration and a fluctuation of a signal can be prevented from occurring during a detection, whereby an inspection can be carried out in a precise manner.

The specimen material detection device in accordance with the present invention is characterized in that the specimen material detection device is a surface plasmon resonance device (an SPR device) or a surface plasmon field enhanced fluorescence spectroscopic measurement device (an SPFS device).

In the case in which the specimen material detection device is a surface plasmon resonance device (an SPR device) or a surface plasmon field enhanced fluorescence spectroscopic measurement device (an SPFS device) as described above, the specimen material detection device is suitable as a detection device of an extremely fine analyte in particular, a reaction efficiency can be improved as compared with a conventional SPR device or a conventional SPFS device, and an SPR device and an SPFS device that are provided with a small variation among individual pieces and a high degree of precision can be implemented.

Advantageous Effects of Invention

The present invention is configured in such a manner that the relationship between the maximum width (a) of the inflow outflow hole and the width (b) of the flow passage is a>b, and an angle θ that is formed between a wall surface of the flow passage and the tangent line of the inflow outflow hole at a contact point of the inflow outflow hole and the flow passage is in the range of 90°≤θ≤135°.

By this configuration, in the case in which after a first solution such as a specimen material solution is made inflow from the inflow outflow hole into the flow passage and the first solution is removed from the flow passage, a second solution is made inflow from the inflow outflow hole into a flow passage, or after a first solution is made inflow from the inflow outflow hole into the flow passage, a second solution is made inflow from the inflow outflow hole into a flow passage via an air that is a driving gas for instance, the first solution can be prevented from remaining at the both ends in a direction of a width near a contact point of the inflow outflow hole and the fine flow passage, whereby a residue of a solution can be prevented, as shown in Table 1 that will be described later, and an irregularity can be prevented from occurring in a concentration and a fluctuation of a signal can be prevented from occurring during a detection, whereby an inspection can be carried out in a precise manner.

The present invention is configured in such a manner that:

for a system in which a distance L from an end part on a side of the flow passage of the inflow outflow hole to a center of the detection region is at least 1 mm, and a solution in which a degree of viscosity at 20° C. is in the range of 1 to 3 mPa*s is sent at an average flow rate in the range of 1 to 5000 μl/min, flow passage length L×variable A<200 (kPa), where the variable A=8×[(flow passage height h+flow passage width b)²×10³/{(flow passage height h×flow passage width b)³×60}], and the units are μl/min for a flow rate, μm for a flow passage height, μm for a flow passage width, μm for a flow passage length, and mPa*s for a degree of viscosity.

As a result, by this configuration, a solution that flows in the flow passage is in the range of a laminar flow region, a turbulent flow does not occur in the flow passage, and a laminar flow causes a uniform flow. Consequently, a stagnation of a solution does not occur in the flow passage. As a result, the detection region in the flow passage is not provided with a disturbance of the index of refraction, and a fluctuation of a signal can be prevented from occurring during a detection, whereby an inspection can be carried out in a precise manner.

BRIEF DESCRIPTION OF THE DRAWINGS

FIG. 5-1 is a schematic view for illustrating a flow of a solution 16 for a specimen material detection device 10 in accordance with the present invention.

FIG. 5-2 is a schematic view for illustrating a flow of a solution 16 for a specimen material detection device 10 in accordance with the present invention.

FIG. 6-1 is a schematic view for illustrating a flow of a solution 16 for a specimen material detection device 10 in accordance with the present invention.

FIG. 6-2 is a schematic view for illustrating a flow of a solution 16 for a specimen material detection device 10 in accordance with the present invention.

FIG. 7-1 is a schematic view for illustrating a flow of a solution 16 for a specimen material detection device 10 in accordance with the present invention.

FIG. 7-2 is a schematic view for illustrating a flow of a solution 16 for a specimen material detection device 10 in accordance with the present invention.

FIG. 8-1 is a schematic view for illustrating a flow of a solution 16 for a specimen material detection device 10 in accordance with the present invention.

FIG. 8-2 is a schematic view for illustrating a flow of a solution 16 for a specimen material detection device 10 in accordance with the present invention.

FIG. 11-1 is a partially enlarged view similar to FIG. 2.

FIG. 11-2 is a partially enlarged view similar to FIG. 2.

DESCRIPTION OF EMBODIMENTS

An embodiment (an example) of the present invention will be described below in detail with reference to the drawings.

Figure 1:
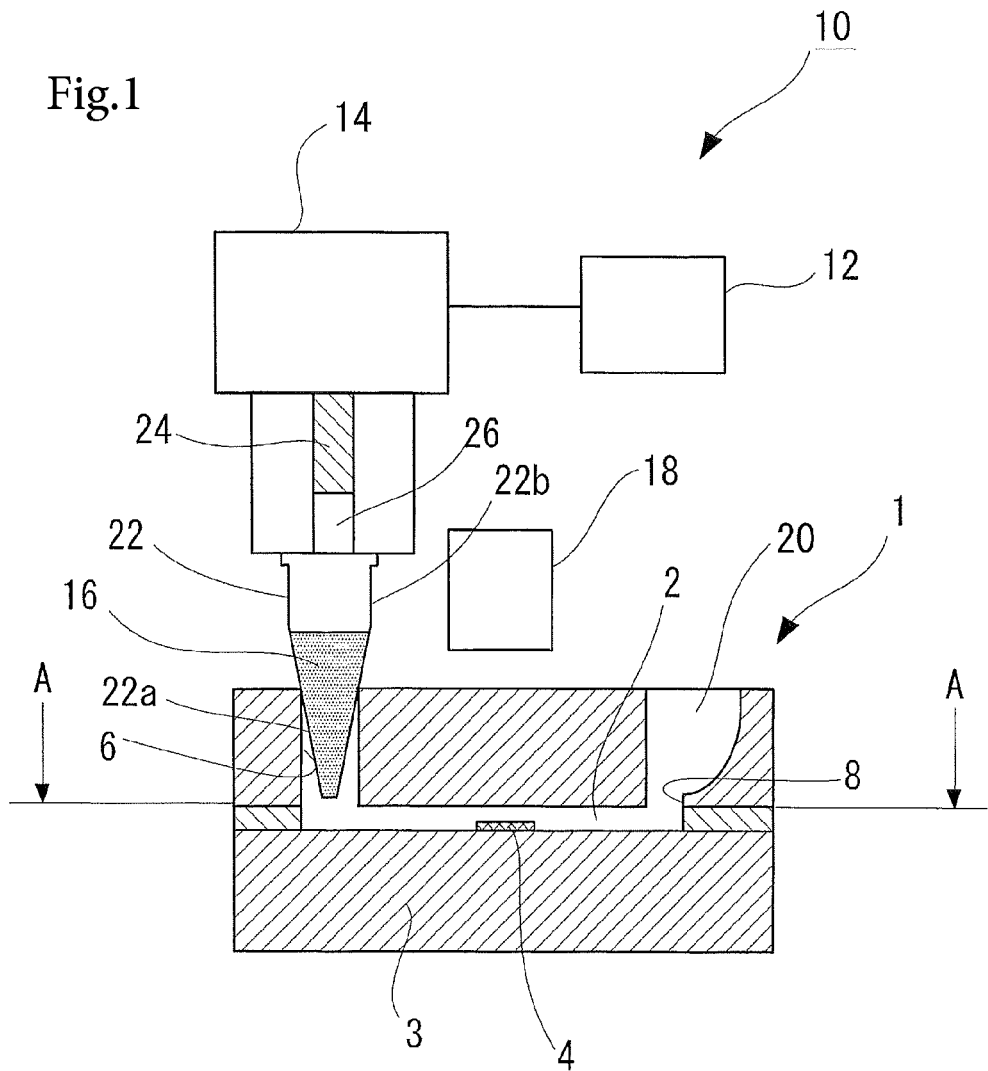
FIG. 1 is a cross sectional view for illustrating a specimen material detection device using a sensor chip in accordance with the present invention.
Figure 2:
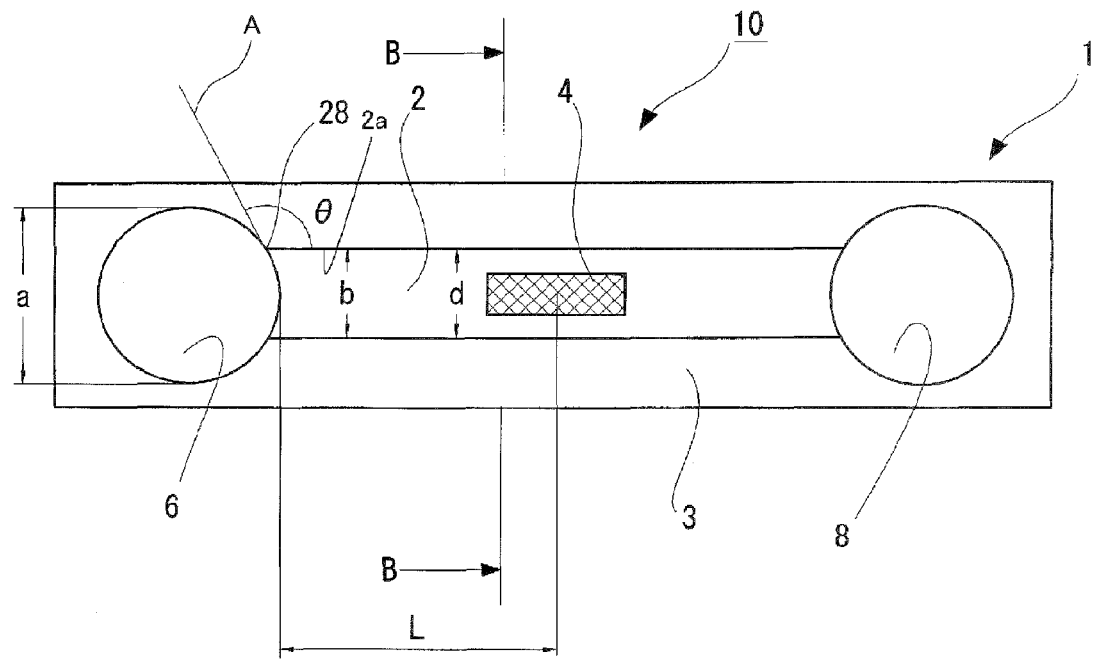
FIG. 2 is an arrow view diagram viewed from a direction of an arrow and taken along the line A-A of FIG. 1.
Figure 3:
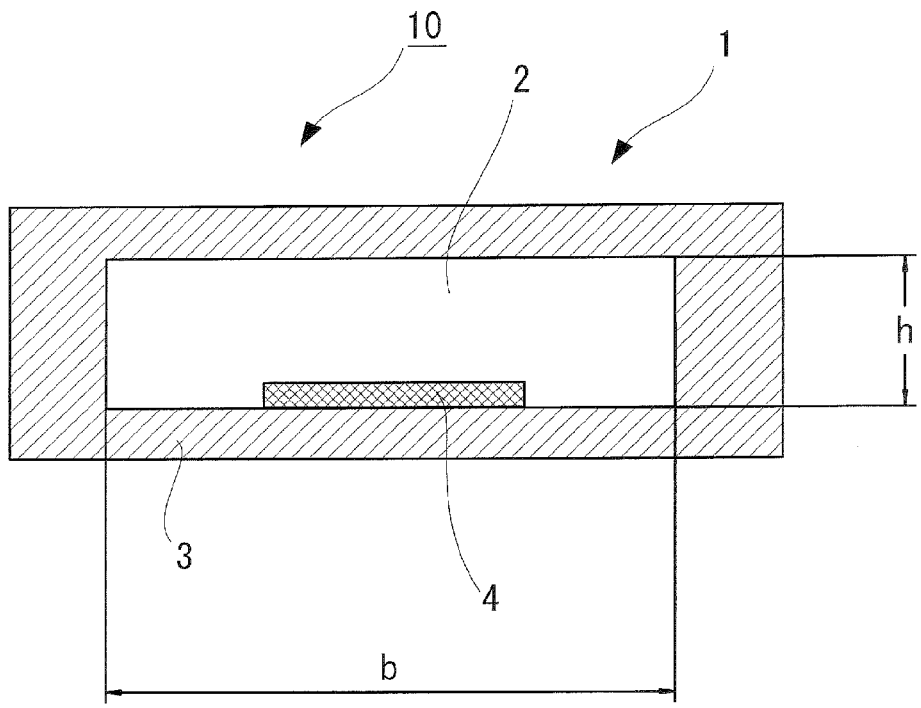
FIG. 3 is an arrow view diagram viewed from a direction of an arrow and taken along the line B-B of FIG. 2.

FIG. 1 is a cross sectional view for illustrating a specimen material detection device using a sensor chip in accordance with the present invention. FIG. 2 is an arrow view diagram viewed from a direction of an arrow and taken along the line A-A of FIG. 1. FIG. 3 is an arrow view diagram viewed from a direction of an arrow and taken along the line B-B of FIG. 2.

As shown in FIG. 1, a symbol 10 represents a specimen material detection device 10 using a sensor chip 1 in accordance with the present invention. The specimen material detection device 10 is provided with the sensor chip 1. The sensor chip 1 is provided with a fine flow passage 2. Inside the fine flow passage 2, a detection region (a reaction field) 4 in a rectangular shape viewed from the top surface is disposed on the bottom surface in the fine flow passage 2 for instance. An antibody of a predetermined amount that reacts with a specific antigen is fixed to the detection region (the reaction field) 4.

The sensor chip 1 is provided with a dielectric member 3 that configures a prism. In addition, a metallic thin film that is not shown is formed on a horizontal top surface of the dielectric member 3, and a detection region 4 is also formed.

The sensor chip 1 is provided with a dielectric member 3 that configures a prism. In addition, a metallic thin film that is not shown is formed on a horizontal top surface of the dielectric member 3, and a detection region 4 is also formed in the present embodiment. However, although it is not shown, it is also possible that a metallic thin film is formed on a substrate, a detection region 4 is formed, and a dielectric member that configures a prism is disposed on the under surface of a substrate so as to be fixed or attached detachably. In this case, the sensor chip 1 means a sensor chip that includes a prism or a sensor chip that does not include a prism.

In the case of the present embodiment, a shape of the detection region 4 is a rectangular shape viewed from the top surface. However, a shape of the detection region 4 can also be a wide variety of shapes such as a circular shape and an ellipse shape.

The sensor chip 1 of the present embodiment is used for a surface plasmon measurement device such as an SPR device and an SPFS device for instance.

As shown in FIG. 2, the fine flow passage 2 is provided with a first inflow outflow hole 6 that is an inflow outflow hole that is configured to make a solution 16 inflow to and outflow from the fine flow passage 2 on an edge part of one side in a direction of the flow passage, and a second inflow outflow hole 8 that is an inflow outflow hole that is configured to make a solution 16 that has been flown from the first inflow outflow hole 6 inflow to and outflow from the fine flow passage 2 on an edge part of the other side in a direction of the flow passage of the fine flow passage 2.

As shown in FIG. 1, a mixing part 20 is connected to the side of a top surface of the second inflow outflow hole 8. The mixing part 20 is formed in a cross sectional shape that is larger than that of the second inflow outflow hole 8, such as a circular shape and a rectangular shape.

As shown in FIG. 1 moreover, a pipette 22 that has held the solution 16 is connected to the side of a top surface of the first inflow outflow hole 6. The pipette 22 is configured so as to be used attachably to and detachably from the first inflow outflow hole 6 of the fine flow passage 2. A diameter of a base end part 22b of the pipette 22 is larger than that of a leading end 22a of the pipette 22.

A solution sending pump 14 is attached to the upper part of the pipette 22. The solution sending pump 14 is communicated with a control part 12. In accordance with a command from the control part 12, the solution 16 that has been held in the pipette 22 can be discharged to the fine flow passage 2 by an operation of a plunger 24 of the solution sending pump 14 via an air (an air damper) 26 that is a driving gas, or the solution 16 that has been stored in the fine flow passage 2 and a mixing part 20 can be sucked to the pipette 22.

By this configuration, in the case in which a solution (a specimen material solution) 16 that includes a specific antigen (analyte) is sent by the solution sending pump 14, the solution 16 passes through the detection region 4 of the fine flow passage 2 in a repetitive manner.

The mixing part 20 is provided with a cross sectional shape that is larger than that of the flow passage of the fine flow passage 2. By this configuration, in the case in which the solution 16 is made inflow into the mixing part 20, a flow of the solution 16 that has been flowing in a laminar flow state becomes turbulent, and the solution 16 that has been stored in the mixing part 20 is stirred.

As a result, even in the case in which the solution 16 passes over the detection region 4 in a repetitive manner, only the same layer does not come into contact with the detection region 4, and most of the solution 16 makes a contribution to a reaction at the detection region 4. Moreover, for the pipette 22, the solution 16 that has been stored is also stirred similarly.

A symbol 18 in FIG. 1 represents a light detection means such as a photomultiplier tube (PMT) and a CCD.

An example of a flowing operation of the solution 16 for the specimen material detection device 10 that is configured as described above will be described with reference to FIGS. 4 to 9.

FIGS. 4 to 9 are the schematic views for illustrating a flow of the solution 16 for the specimen material detection device 10 in accordance with the present invention.

The arrows of FIGS. 4 to 9 indicate a solution sending direction of the solution 16. A symbol S represents an interfacial boundary surface on the side of a back end in a direction of a solution sending between the solution 16 and an air, that is, an air liquid interface, and a symbol T represents an interfacial boundary surface on the side of a front end in a direction of a solution sending between the solution 16 and an air, that is, an air liquid interface.

Figure 4:
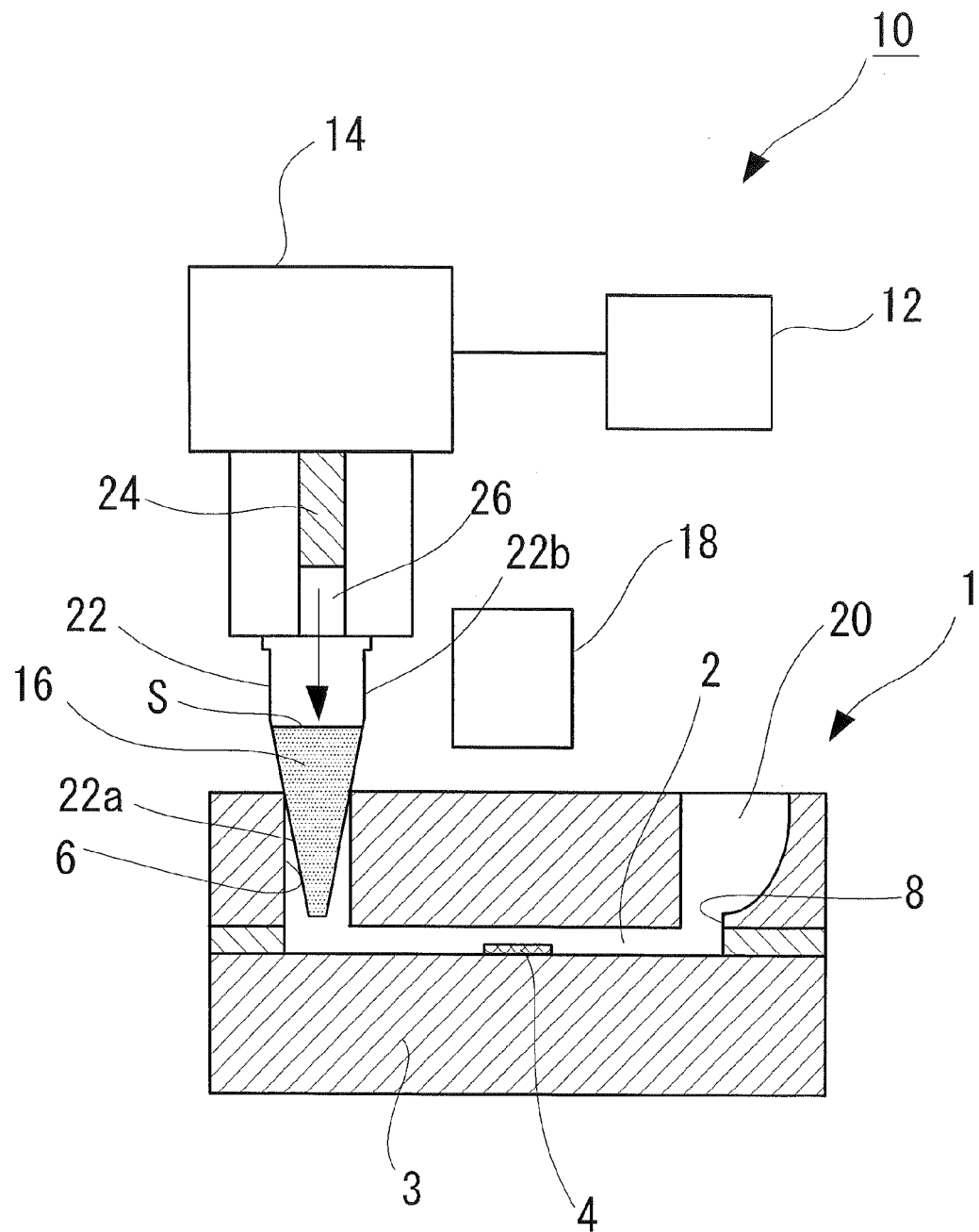
FIG. 4 is a schematic view for illustrating a flow of a solution 16 for a specimen material detection device 10 in accordance with the present invention.

FIG. 4 shows the state in which the pipette 22 that holds the solution 16 is mounted to the first inflow outflow hole 6 of the fine flow passage 2 and the solution sending pump 14 is attached to the pipette 22.

Figures 1, 5:
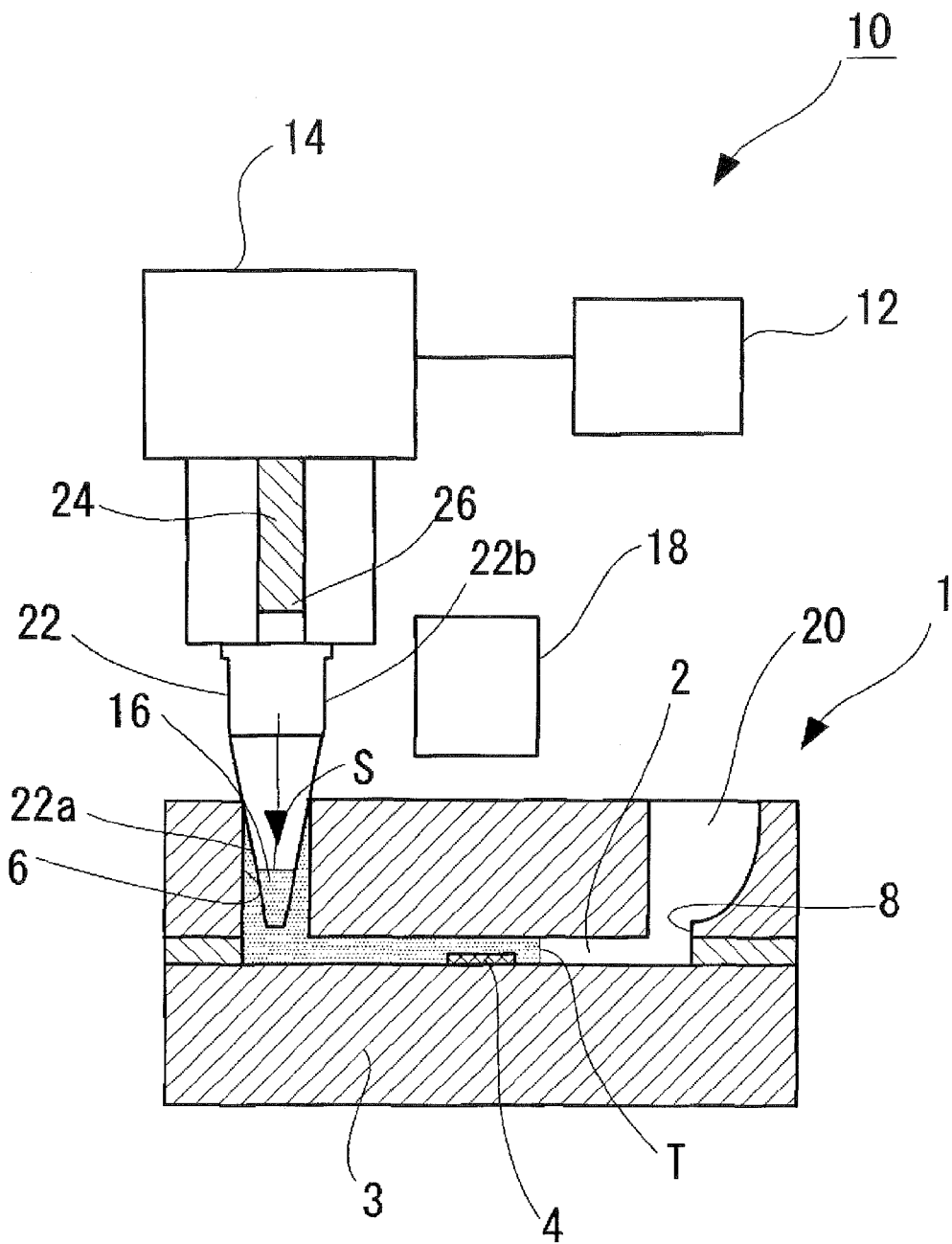
Figures 2, 5:
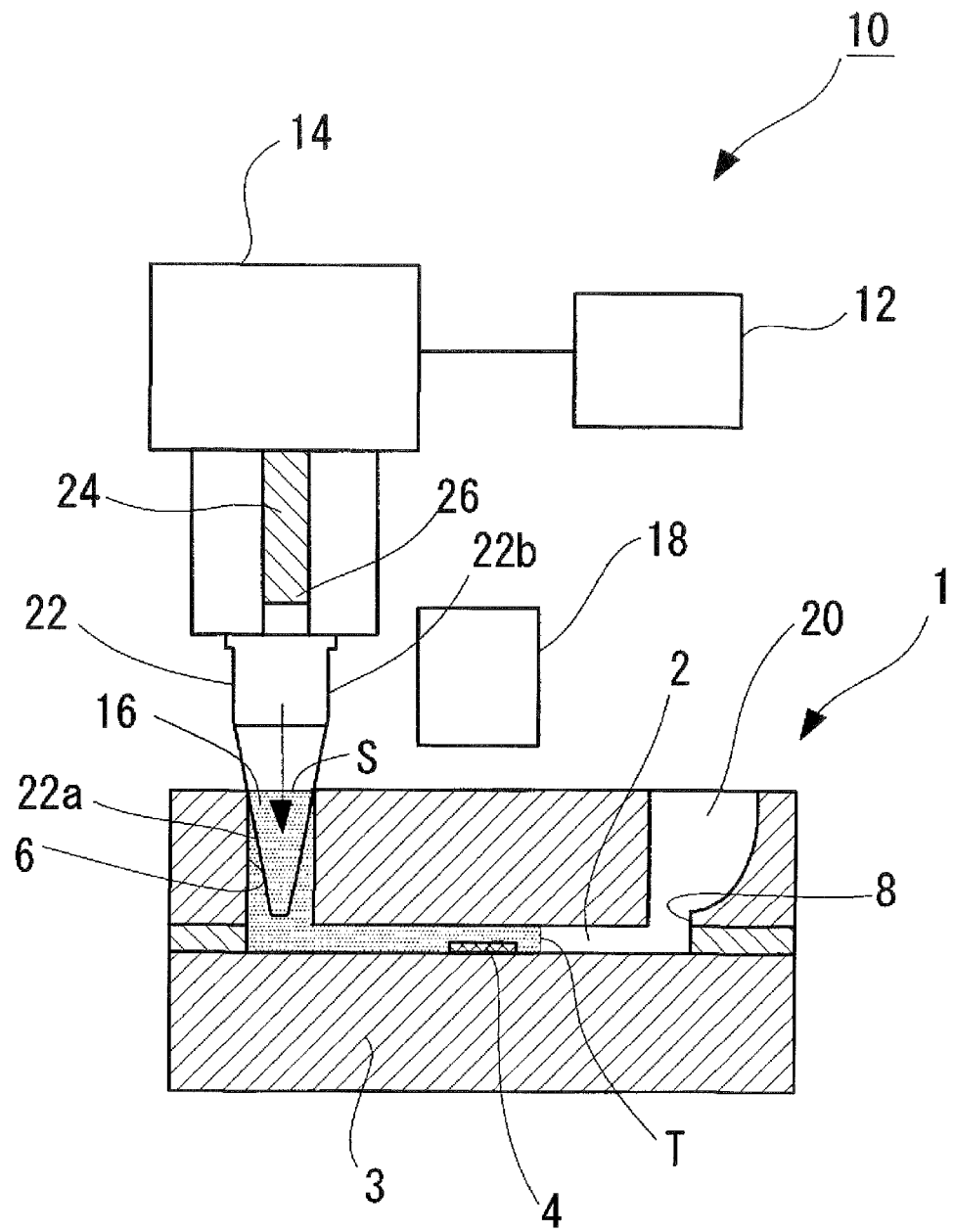

In the case in which the solution sending pump 14 is driven and the solution 16 that has been held in the pipette 22 is discharged as shown by the arrow in the state shown in FIG. 4, the solution 16 is made inflow into the fine flow passage 2 via the first inflow outflow hole 6 and a part of the solution 16 passes over the detection region 4 as shown in FIG. 5-1.

Figures 1, 6:
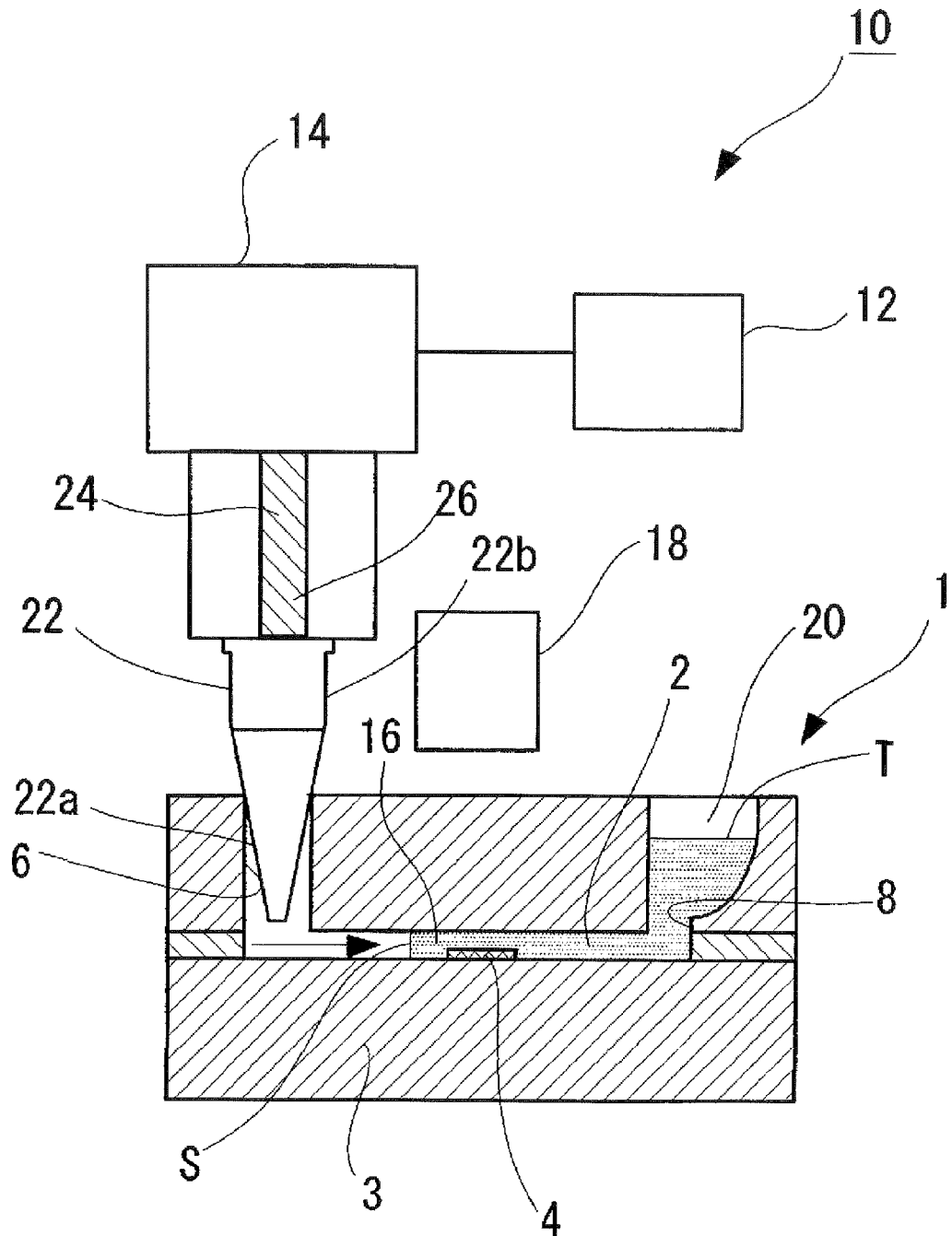
Figures 2, 6:
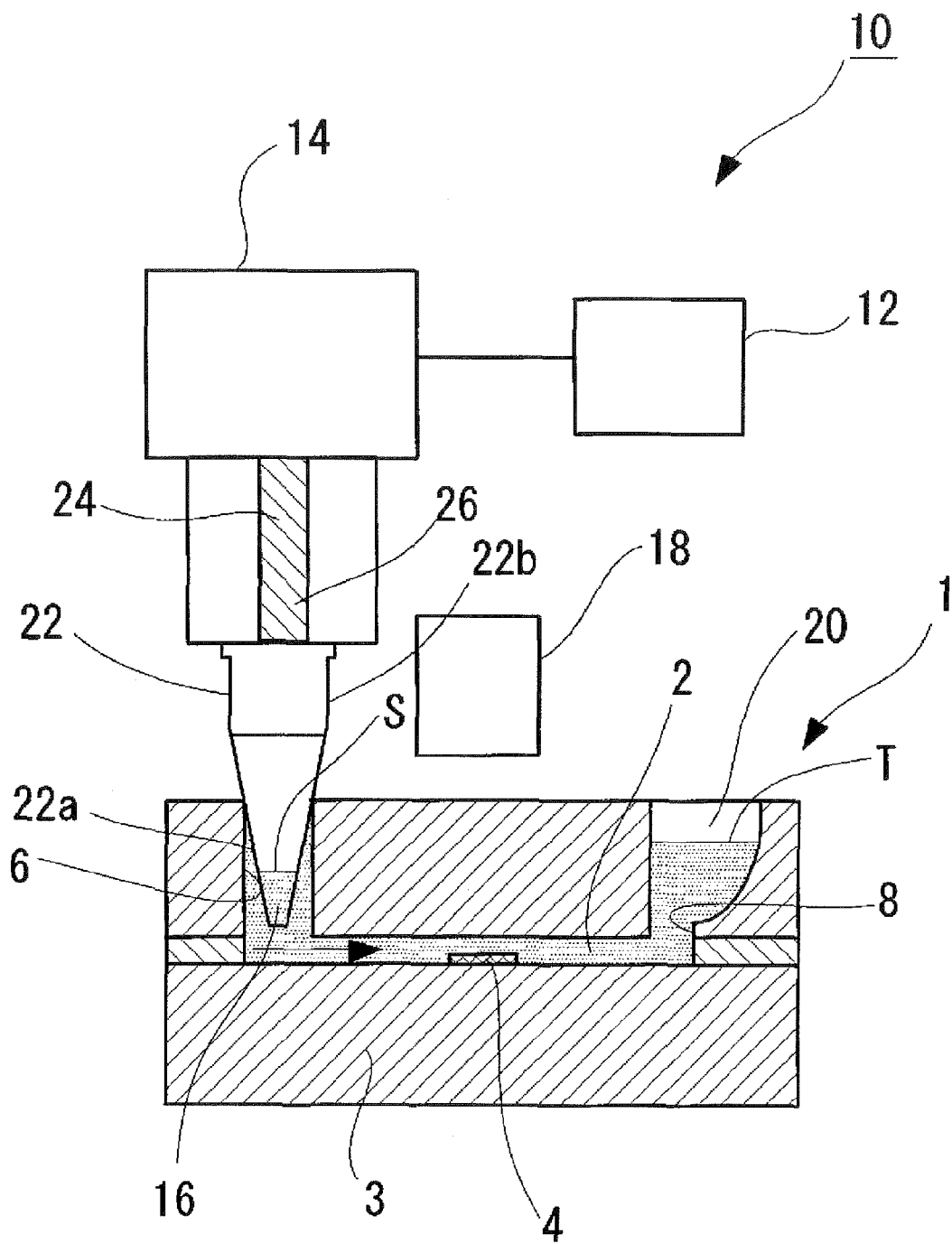

In the case in which the solution sending pump 14 further discharges the solution 16 that has been held in the pipette 22 from this state, the most of the solution 16 in the pipette 22 is made inflow into the fine flow passage 2 via the first inflow outflow hole 6 and an air liquid interface S is located between the first inflow outflow hole 6 of the fine flow passage 2 and the detection region 4 as shown in FIG. 6-1. In addition, the solution 16 that has passed over the detection region 4 is flown into the mixing part 20 via the second inflow outflow hole 8, and an air liquid interface T in the mixing part 20 moves upward.

The solution sending pump 14 is then driven in order to suck the solution 16 in this state.

Figures 1, 7:
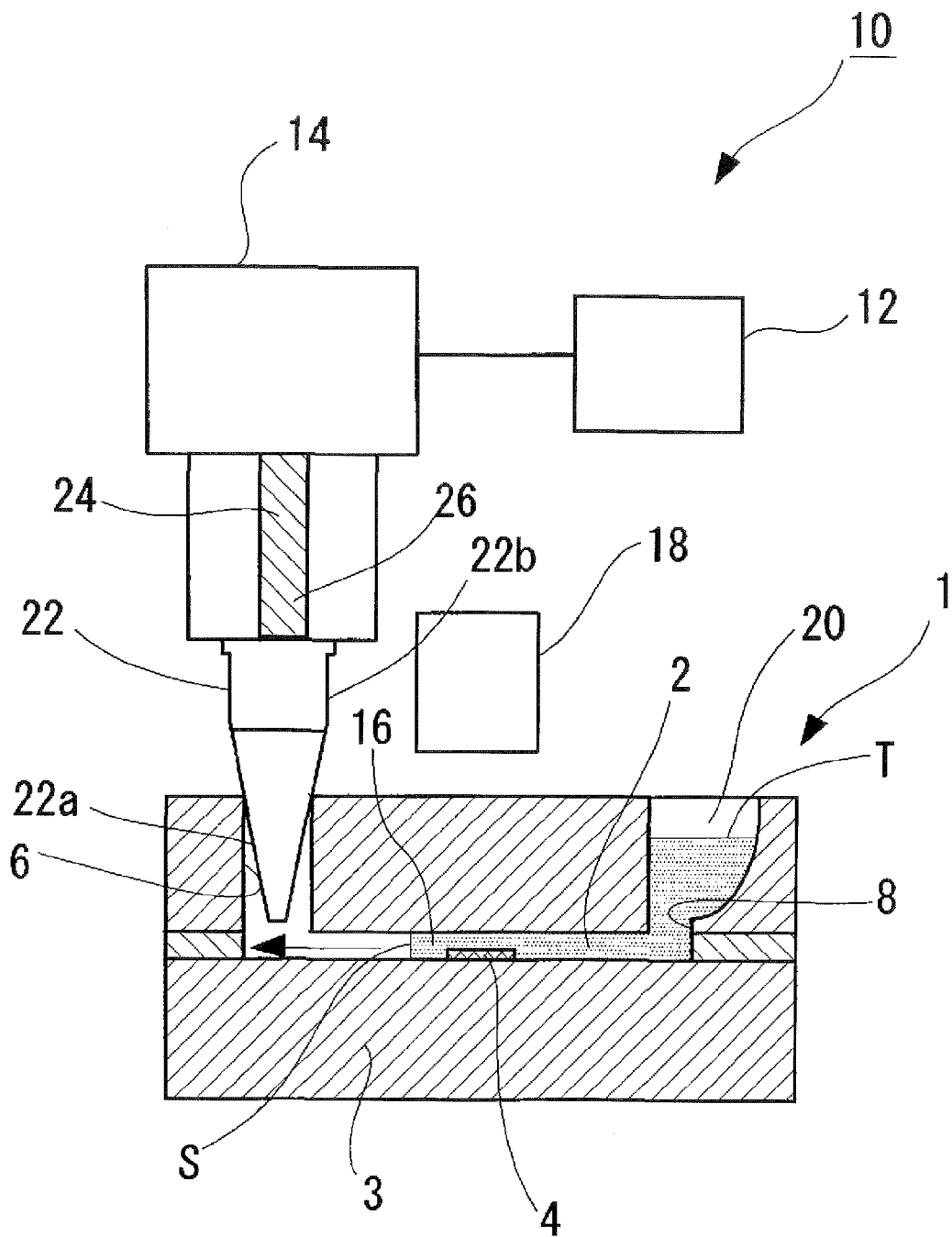
Figures 2, 7:
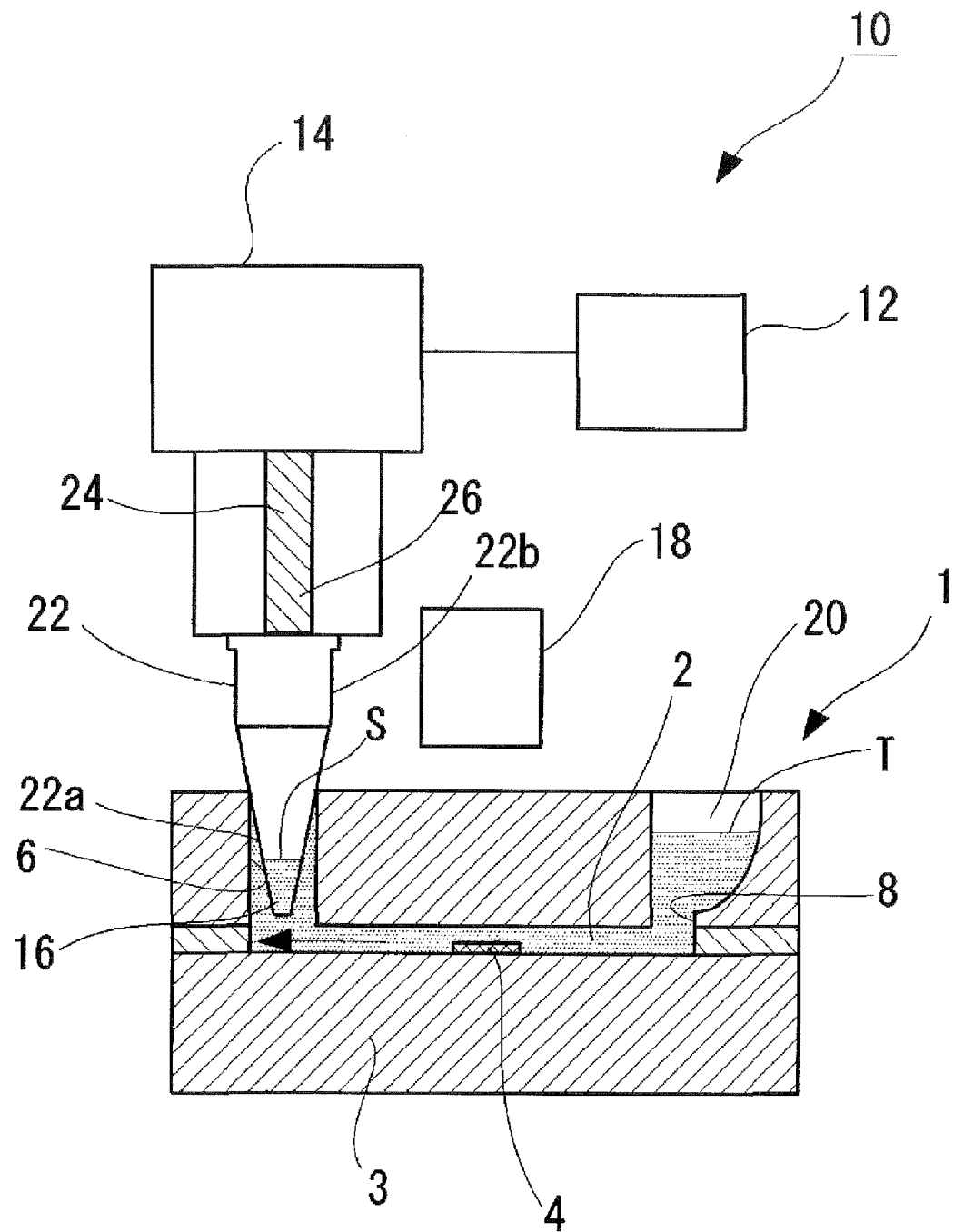

By this operation, a solution sending direction of the solution 16 is then reversed as shown by the arrow in FIG. 7-1. The solution 16 in the mixing part 20 is then made inflow into the fine flow passage 2 via the second inflow outflow hole 8, passes over the detection region 4 again, and is made inflow into the pipette 22 via the first inflow outflow hole 6. An air liquid interface S in the pipette 22 moves upward, and an air liquid interface T in the fine flow passage 2 is located near the detection region 4 as shown in FIG. 8-1.

Figures 1, 8:
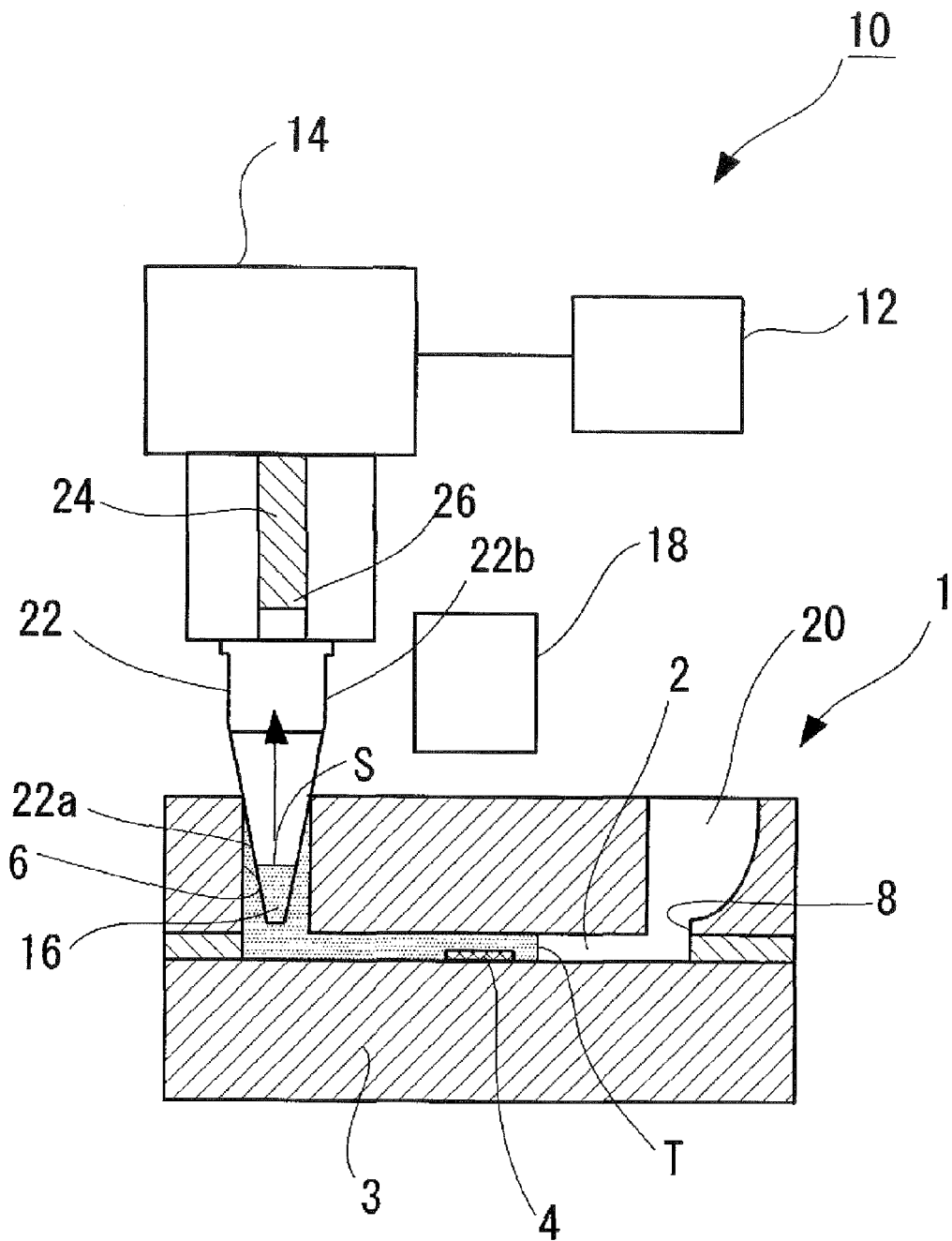
Figures 2, 8:
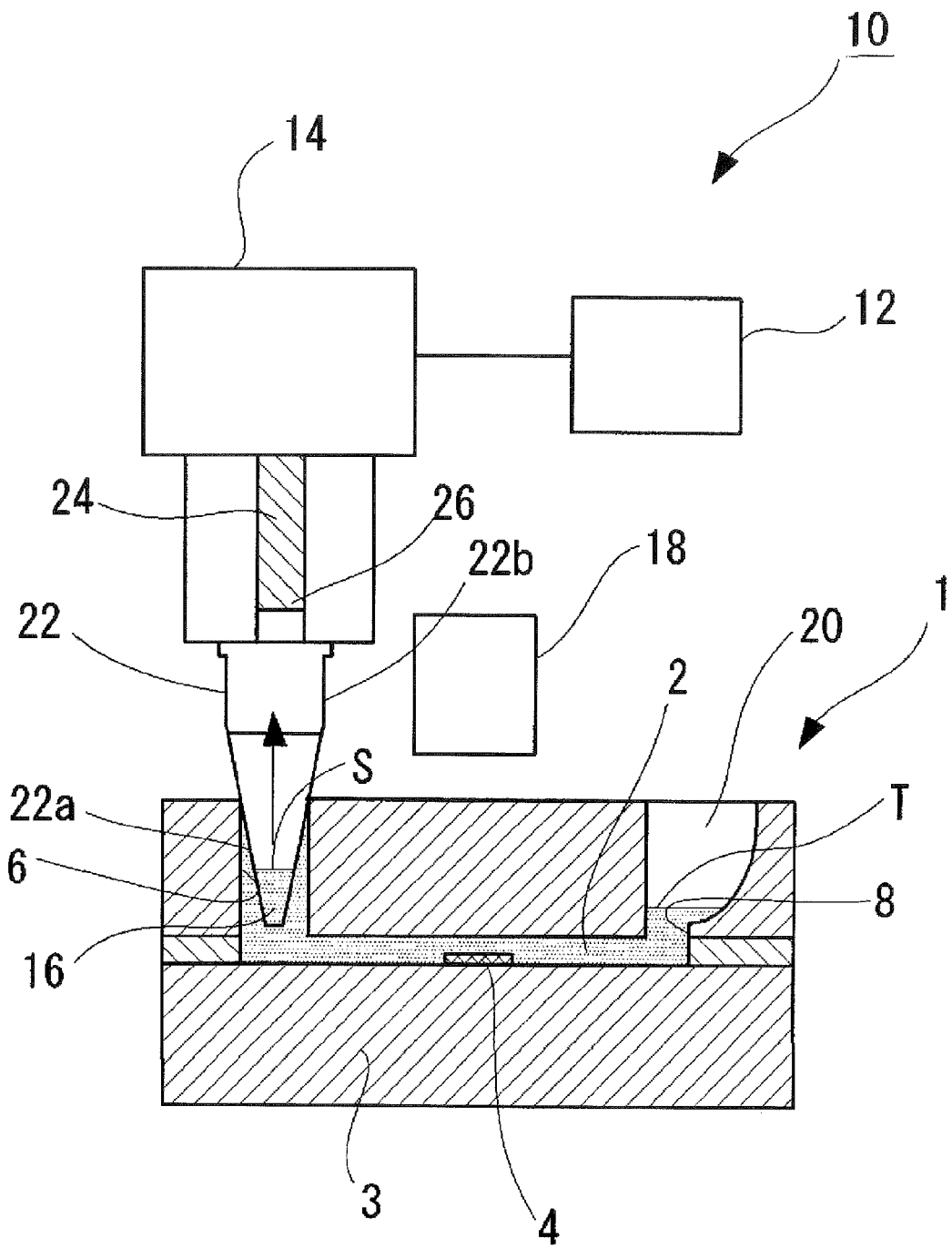

The solution sending pump 14 is then driven in order to discharge the solution 16 again in the state shown in FIG. 8-1. By this operation, a solution sending direction of the solution 16 is then reversed again. The solution 16 in the pipette 22 is then made inflow into the fine flow passage 2 via the first inflow outflow hole 6, and the solution 16 that has passed over the detection region 4 is made inflow into the mixing part 20 via the second inflow outflow hole 8 in the state shown in FIG. 6-1.

Figure 9:
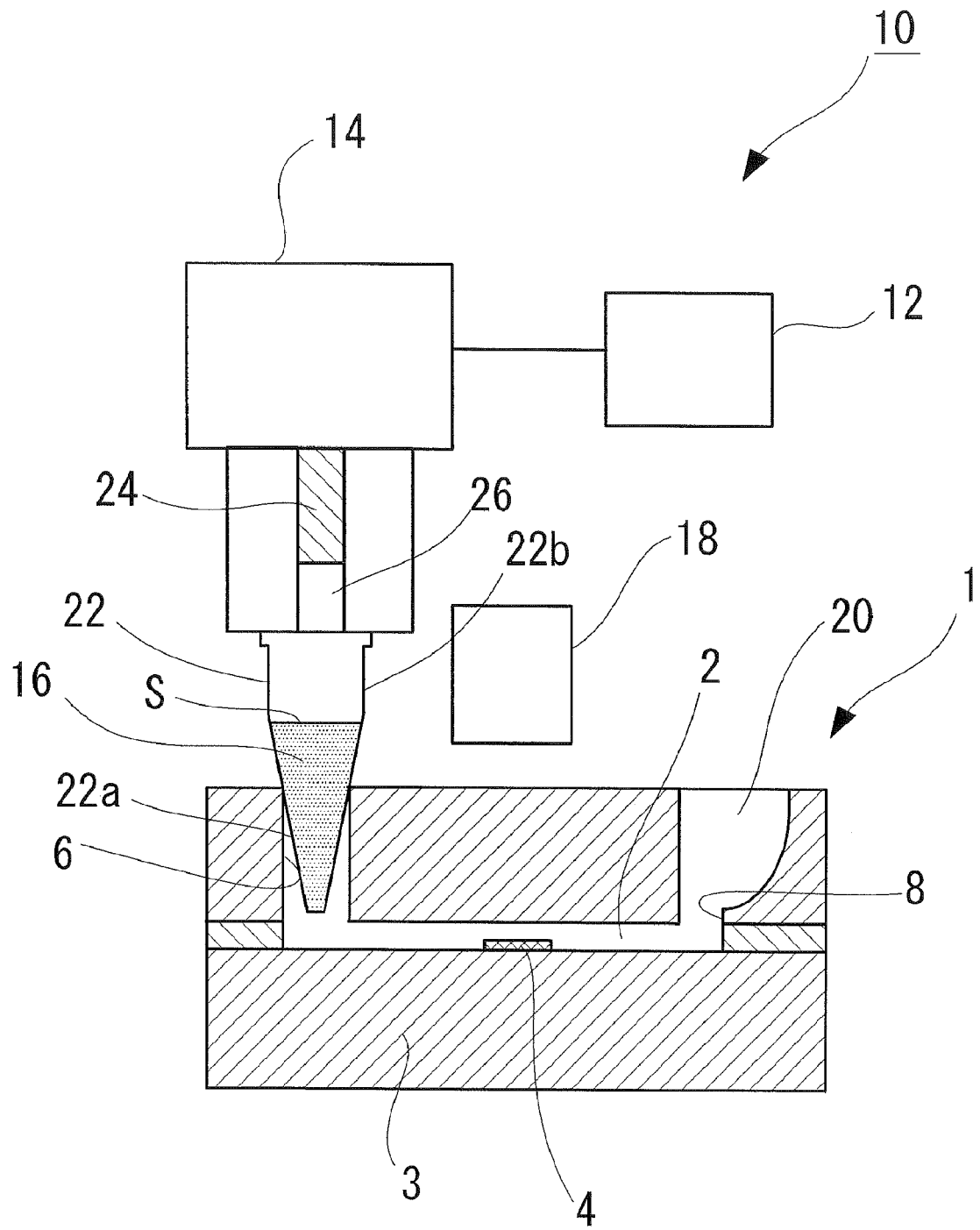
FIG. 9 is a schematic view for illustrating a flow of a solution 16 for a specimen material detection device 10 in accordance with the present invention.

In the case in which the solution 16 is recovered, after the solution sending pump 14 performs a suction of the solution 16 to the state shown in FIG. 9, the pipette 22 that holds the solution 16 can be detached.

For the specimen material detection device 10 in accordance with the present embodiment as described above, the states of FIG. 6-1, FIG. 7-1, FIG. 8-1, and FIG. 6-1 are transferred in a repetitive manner by operating the discharge and the suction using the solution sending pump 14 in a repetitive manner, whereby the solution 16 passes over the detection region 4 in the fine flow passage 2 in a repetitive manner.

In addition to the method of a solution sending for the solution 16 for the specimen material detection device 10 as described above, the following method of a solution sending can also be carried out as shown in FIGS. 5-2 to 8-2.

In other words, a method of a solution sending can also be adopted for sending a solution in a state in which an interfacial boundary surface (the air liquid interface S) on the side of a back end in a direction of a solution sending between the solution 16 and an air and an interfacial boundary surface (the air liquid interface T) on the side of a front end in a direction of a solution sending between the solution 16 and an air are located in the pipette 22 and in the mixing part 20 on a constant basis.

This is because an accurate measurement cannot be carried out since an air bubble is generated when an air liquid interface passes through a region that becomes narrow in the case in which a solution that includes a protein or a surface activating agent is sent.

More specifically, it is preferable that the following method of a solution sending is carried out.

In the case in which the solution sending pump 14 is driven and the solution 16 that has been held in the pipette 22 is discharged as shown by the arrow in the state shown in FIG. 4, the solution 16 is made inflow into the fine flow passage 2 via the first inflow outflow hole 6 and a part of the solution 16 passes over the detection region 4 as shown in FIG. 5-2.

In this case as shown in FIG. 5-2, an interfacial boundary surface (the air liquid interface S) on the side of a back end in a direction of a solution sending between the solution 16 and an air is located in the pipette 22 on a constant basis.

In the case in which the solution sending pump 14 further discharges the solution 16 that has been held in the pipette 22 from this state, the solution 16 is made inflow into the fine flow passage 2 via the first inflow outflow hole 6 and an air liquid interface S is located near a leading end in the pipette 22 as shown in FIG. 6-2. In addition, the solution 16 that has passed over the detection region 4 is flown into the mixing part 20 via the second inflow outflow hole 8, and an air liquid interface T in the mixing part 20 moves upward.

Even in this state as shown in FIG. 6-2, an interfacial boundary surface (the air liquid interface S) on the side of a back end in a direction of a solution sending between the solution 16 and an air is located in the pipette 22 on a constant basis. Moreover, an interfacial boundary surface (the air liquid interface T) on the side of a front end in a direction of a solution sending between the solution 16 and an air is located in the mixing part 20 on a constant basis.

The solution sending pump 14 is then driven in order to suck the solution 16 in this state.

By this operation, a solution sending direction of the solution 16 is then reversed as shown by the arrow in FIG. 7-2. The solution 16 in the mixing part 20 is then made inflow into the fine flow passage 2 via the second inflow outflow hole 8, passes over the detection region 4 again, and is made inflow into the pipette 22 via the first inflow outflow hole 6.

An air liquid interface S in the pipette 22 then moves upward, and an air liquid interface T is located near the lower end in the mixing part 20 as shown in FIG. 8-2.

Even in the state shown in FIGS. 7-2 and 8-2, an interfacial boundary surface (the air liquid interface S) on the side of a back end in a direction of a solution sending between the solution 16 and an air is located in the pipette 22 on a constant basis. Moreover, an interfacial boundary surface (the air liquid interface T) on the side of a front end in a direction of a solution sending between the solution 16 and an air is located in the mixing part 20 on a constant basis.

The solution sending pump 14 is then driven in order to discharge the solution 16 again in the state shown in FIG. 8-2. By this operation, a solution sending direction of the solution 16 is then reversed again. The solution 16 in the pipette 22 is then made inflow into the fine flow passage 2 via the first inflow outflow hole 6, and the solution 16 that has passed over the detection region 4 is made inflow into the mixing part 20 via the second inflow outflow hole 8 in the state shown in FIG. 6-2.

In the case in which the solution 16 is recovered, after the solution sending pump 14 performs a suction of the solution 16 to the state shown in FIG. 9, the pipette 22 that holds the solution 16 can be detached.

For the specimen material detection device 10 in accordance with the present embodiment as described above, the states of FIG. 6-2, FIG. 7-2, FIG. 8-2, and FIG. 6-2 are transferred in a repetitive manner by operating the discharge and the suction using the solution sending pump 14 in a repetitive manner, whereby the solution 16 passes over the detection region 4 in the fine flow passage 2 in a repetitive manner.

During such a solution sending in a reciprocated manner, an interfacial boundary surface (the air liquid interface S) on the side of a back end in a direction of a solution sending between the solution 16 and an air and an interfacial boundary surface (the air liquid interface T) on the side of a front end in a direction of a solution sending between the solution 16 and an air are located in the pipette 22 or in the mixing part 20 on a constant basis.

An accurate measurement cannot be carried out since an air bubble is generated when an air liquid interface passes through a region that is narrow in the case in which a solution that is easy to foam, such as a solution that includes a protein solution or a surface activating agent, is sent. The above configuration can prevent the above problem.

Figure 24:
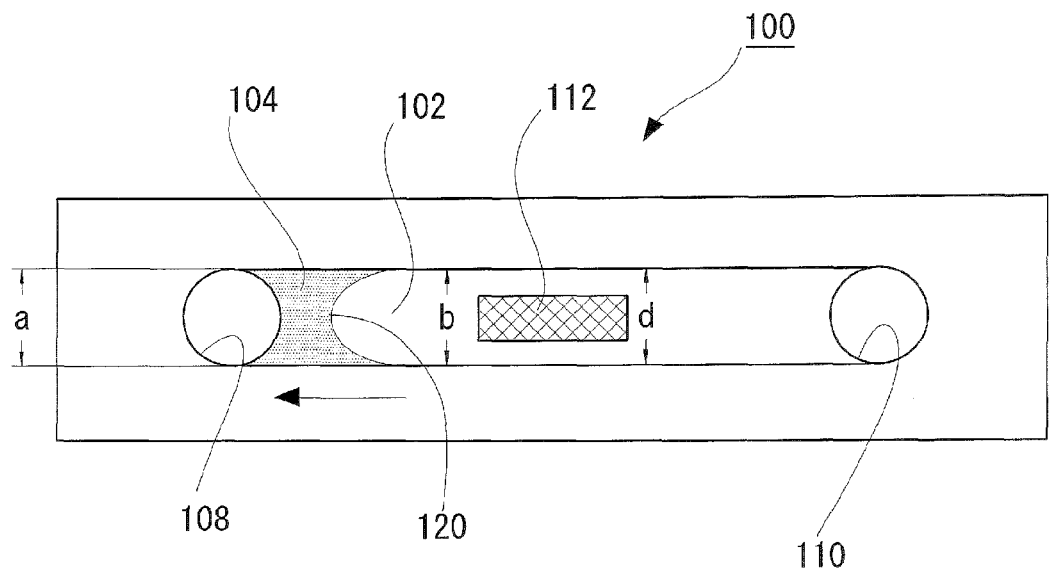
FIG. 24 is an arrow view diagram viewed from a direction of an arrow and taken along the line A-A of FIG. 23 for illustrating a flow of a solution.

By the way, as described for the conventional specimen material detection device 100, as shown in FIG. 24, in the case in which a width b of the fine flow passage 102 that comes into contact with the inflow outflow hole 108 is equal to or larger than the maximum width a of the inflow outflow hole 108 (a diameter a of the inflow outflow hole 108 in this case), when the first solution 104 is discharged from the inflow outflow hole 108, a flow rate is low at a wall surface of the fine flow passage 102 and a flow rate is high at the center part in a direction of a width of the first solution 104 in the fine flow passage 102 unfortunately.

Figure 25:
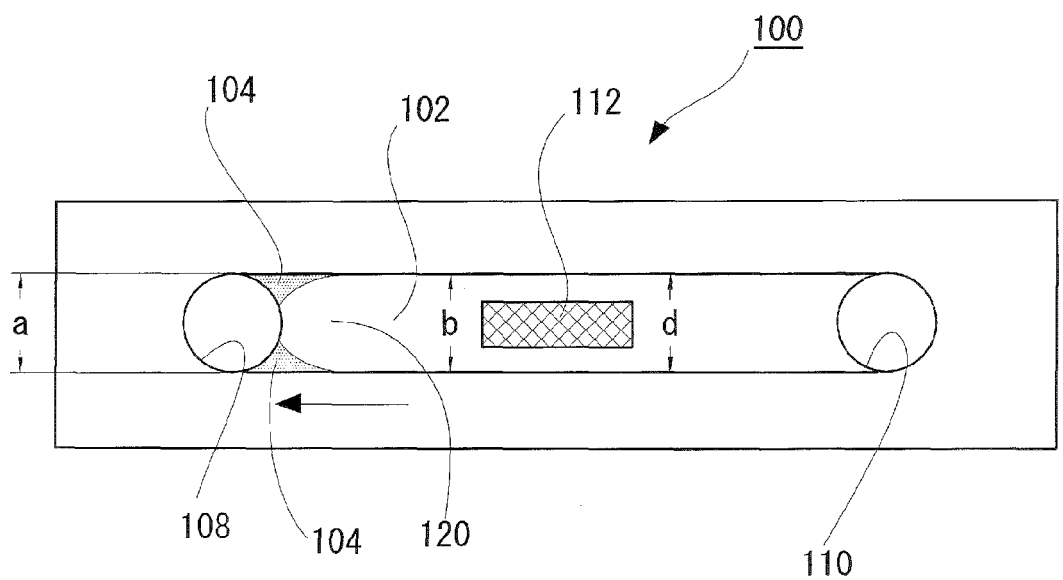
FIG. 25 is an arrow view diagram viewed from a direction of an arrow and taken along the line A-A of FIG. 23 for illustrating a flow of a solution.

Consequently, as shown in FIG. 25, a solution back end 120 at the center part in a direction of a width of the first solution 104 in the fine flow passage 102 reaches the inflow outflow hole 108 at first, and the first solution 104 remains at the both ends in a direction of a width near a contact point of the inflow outflow hole 108 and the fine flow passage 102, thereby causing a residue of a solution.

In particular, in the case of a sandwich assay in which a cleaning solution, a specimen material solution, a cleaning solution, and a reaction test reagent are made inflow in this order into the fine flow passage 102, in the case in which the previous solution remains, the next test reagent is diluted. As a result, an irregularity occurs in a concentration and a fluctuation of a signal occurs during a detection, whereby the detection accuracy is deteriorated.

Consequently, for a mechanism that is configured to carry out an assay in a flow passage with a minute sample as described above, a shape of a flow passage has a deep relationship with a fluctuation of a measurement.

Therefore, as shown in FIG. 2, the present invention is configured in such a manner that the relationship between the maximum width (a) of the first inflow outflow hole 6 and the width (b) of the fine flow passage 2 is a>b, where the maximum width (a) is the maximum length in a direction that is equivalent to a direction of a width of a flow passage.

Moreover, as shown in FIG. 2, the present invention is configured in such a manner that an angle θ that is formed between a wall surface 2a of the fine flow passage 2 and the tangent line A of the first inflow outflow hole 6 at a contact point 28 of the first inflow outflow hole 6 and the fine flow passage 2 is in the range of 90°≤θ≤135°.

Figure 10:
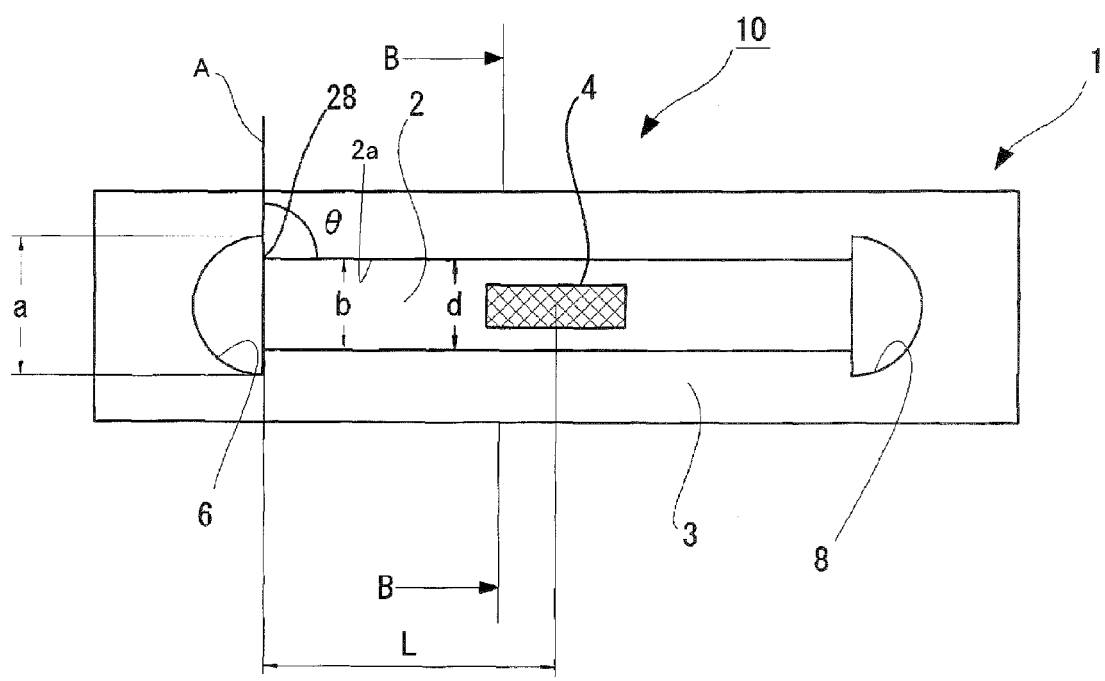
FIG. 10 is a partially enlarged view similar to FIG. 2.
Figures 1, 11:
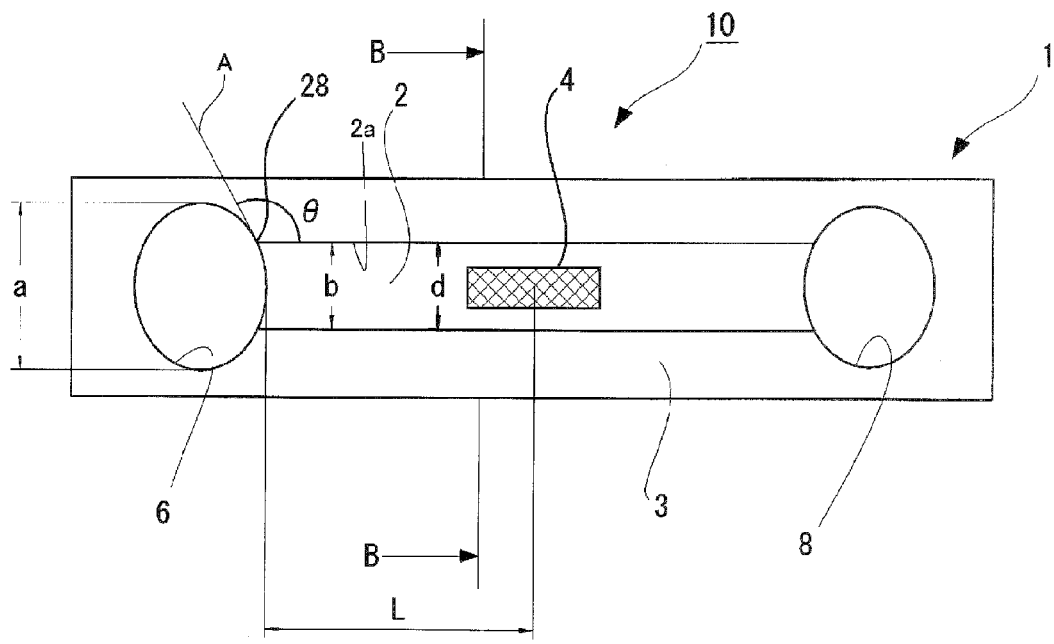
Figures 2, 11:
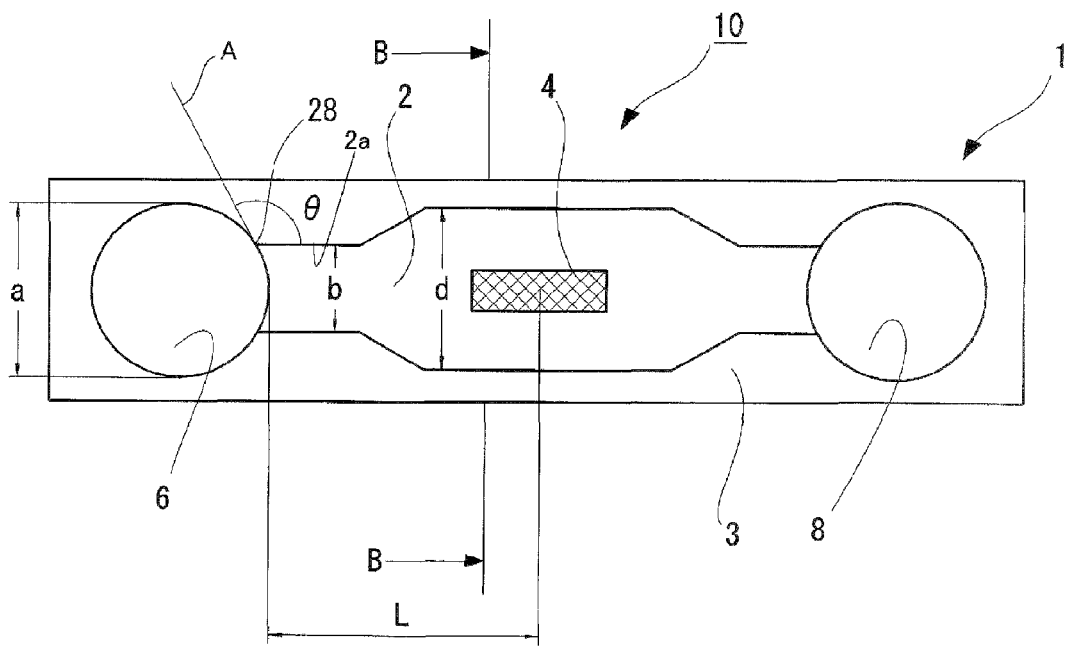

In the present embodiment, a cross sectional shape of the first inflow outflow hole 6 is a circular shape. However, a cross sectional shape of the first inflow outflow hole 6 can also be a semicircular shape (in the case of θ=90°), a quadrangular shape (in the case of θ=90°), and a shape of an ellipse as shown in FIGS. 10 and 11-1.

In the present embodiment, a width (b) of the fine flow passage 2 is constant. However, it is also possible that a detection area region width (d) of a detection region (a reaction field) 4 is formed so as to be larger than the width (b) of the fine flow passage 2 as shown in FIG. 11-2.

By this configuration, in the case in which after a first solution 16 such as a specimen material solution is made inflow from the first inflow outflow hole 6 and the first solution 16 is removed from the first inflow outflow hole 6, another second solution is made inflow into the fine flow passage 2, or another second solution is made inflow into the fine flow passage 2 via an air (an air damper) 26 that is a driving gas for instance, as shown in Table 1, the first solution 16 can be prevented from remaining at the both ends in a direction of a width near a contact point 28 of the first inflow outflow hole 6 and the fine flow passage 2, whereby a residue of a solution can be prevented, and an irregularity can be prevented from occurring in a concentration and a fluctuation of a signal can be prevented from occurring during a detection, whereby an inspection can be carried out in a precise manner.

In other words, in Table 1, in the case in which the maximum width (a) of the first inflow outflow hole 6 (a diameter (a) of an interface (IF)) and the width (b) of the fine flow passage 2 (a width (b) of a flow passage that comes into contact with an interface (IF)) are equivalent to each other, it can be found that a residual amount of a solution is large and a fluctuation of a signal occurs during a detection (a variation coefficient CV value is large).

Moreover, even in the case in which the relationship between the maximum width (a) of the first inflow outflow hole 6 and the width (b) of the fine flow passage 2 is a>b, when an angle θ that is formed between a wall surface 2a of the fine flow passage 2 and the tangent line A of the first inflow outflow hole 6 exceeds 135° as shown in Table 1, a residual amount of a solution is large and a fluctuation of a signal occurs during a detection (a variation coefficient CV value is large). In addition, in the case in which an angle θ that is formed between a wall surface 2a of the fine flow passage 2 and the tangent line A of the first inflow outflow hole 6 is lower than 90°, a residue of a solution occurs near the first inflow outflow hole 6, a residual amount of a solution is large, and a fluctuation of a signal occurs during a detection (a variation coefficient CV value is large).

On the other hand, an angle θ that is formed between a wall surface 2a of the fine flow passage 2 and the tangent line A of the first inflow outflow hole 6 is in the range of 90°≤θ≤135° as shown in Table 1, it can be found that a residual amount of a solution is small and a fluctuation of a signal can be prevented from occurring during a detection (a variation coefficient CV value is small).

TABLE 1

| IF diameter (mm) | Flow passage width b (mm) | Width of a detection region (mm) | Angle θ (°) | Residual amount of a solution (μl) | Average value of a signal | Standard deviation | Variation coefficient CV (%) |
|---|---|---|---|---|---|---|---|
| 3 | 3 | 3 | 180 | 4~14 | 425894 | 16731 | 3.9 |
| 1 | 1 | 3 | 180 | 1~9 | 436863 | 14863 | 3.4 |
| 1.2 | 1 | 3 | 146 | 2~11 | 430460 | 14537 | 3.4 |
| 1.38 | 1 | 3 | 136 | 2.7~9.3 | 431503 | 12837 | 3.0 |
| 1.41 | 1 | 3 | 135 | 3~5.8 | 437911 | 4433 | 1.0 |
| 1.5 | 1 | 3 | 132 | 2.8~5.2 | 440352 | 4523 | 1.0 |
| 3 | 1 | 3 | 109 | 2.9~4.1 | 443305 | 2169 | 0.5 |
| 5 | 1 | 3 | 102 | 3~4.5 | 441854 | 2397 | 0.5 |
| 3 | 1 | 3 | 90 | 2.9~4.2 | 443389 | 2660 | 0.6 |

Table 1 shows the case in which an inspection has been carried out using a sample of 100 ml five times under each condition.

For the present invention, it is preferable that:

for a system in which a distance L from an end part on a side of the flow passage of the first inflow outflow hole 6 to a center of the detection region 4 is at least 1 mm, and a solution in which a degree of viscosity at 20° C. is in the range of 1 to 3 mPa*s is sent at an average flow rate in the range of 1 to 5000 μl/min, flow passage length L×variable A<200 (kPa), where the variable A=8×[(flow passage height h+flow passage width b)$^2$×10$^3$/{(flow passage height h×flow passage width b)$^3$×60}], and the units are μl/min for a flow rate, μm for a flow passage height, μm for a flow passage width, μm for a flow passage length, and mPa*s for a degree of viscosity.

Here, an average flow rate is calculated by a time from a start of a movement of a solution by a solution sending to a stop of a movement of a solution and an amount of a solution that has been moved. In the case in which a cross sectional area of a flow passage is constant, "an amount of a solution that has been moved" can be calculated from an amount of a movement of a solution by the image analysis. Moreover, a flow rate instrument can also be used. Furthermore, "a time from a start of a movement of a solution to a stop of a movement of a solution" can also be obtained by the image analysis for instance.

In other words, in the case in which a distance L from an end part on a side of the flow passage of the first inflow outflow hole 6 to a center of the detection region 4 is too short for the fine flow passage 2 that comes into contact with the first inflow outflow hole 6, a flow of a solution that has just flown from the first inflow outflow hole 6 is turbulent. In addition, in the case in which a solution that is measured stagnates, a disturbance occurs for the index of refraction. Consequently, for the SPR device and the SPFS device in which the index of refraction has a huge effect on the accuracy of an inspection, the large variations have a huge effect on the accuracy of a measurement in the case in which a measurement is carried out.

Consequently, it is necessary that a location of the detection region 4 in the fine flow passage 2 is set apart by a constant distance from the first inflow outflow hole 6 and a measurement is carried out at a location in which a flow of a solution 16 is stable.

However, even in the case in which a distance L from an end part on a side of the flow passage of the first inflow outflow hole 6 to a center of the detection region 4 is too long, the configuration creates an adverse result.

In other words, the relationship between the maximum width (a) of the first inflow outflow hole 6 and the width (b) of the fine flow passage 2 is a>b and a flow passage height is small as described above. Consequently, in the case in which a distance L is set to be long, a resistance of the flow passage becomes large. Therefore, in the case in which a resistance of the flow passage becomes large, a pressure that is applied during a solution sending becomes large. As a result, a leakage of a solution occurs from the first inflow outflow hole 6 or a junction part 28 of the first inflow outflow hole 6 and the fine flow passage 2.

In particular, for the configuration of a solution sending that is provided with an air (an air damper) 26 that is a driving gas in a solution sending system, in addition to a leakage of a solution, a movement of a plunger 24 and an amount of a solution that is sent do not keep pace with each other and a speed of the plunger 24 and a rate of a solution sending vary more greatly in the case in which a resistance in the fine flow passage 2 is larger. As a result, a desired amount of a solution cannot be sent, a sensitivity of a measurement is degraded, and a fluctuation of a measurement becomes larger.

Consequently, it is not preferable that a distance L is too long from the aspect of the performance of a solution sending and a fluctuation of a measurement. Moreover, it is also not preferable that a distance L is too short from the aspect of a fluctuation of a measurement caused by a turbulence of a solution.

As a result, like the configuration of the present invention, it is preferable that:

for a system in which a distance L from an end part on a side of the flow passage of the first inflow outflow hole 6 to a center of the detection region 4 is at least 1 mm, and a solution in which a degree of viscosity at 20° C. is in the range of 1 to 3 mPa*s is sent at an average flow rate in the range of 1 to 5000 μl/min, flow passage length L×variable A<200 (kPa), where the variable $A=8\times[(\text{flow passage height h}+\text{flow passage width b})^2\times10^3/\{(\text{flow passage height h}\times\text{flow passage width b})^3\times60\}]$, and the units are μl/min for a flow rate, μm for a flow passage height, μm for a flow passage width, μm for a flow passage length, and mPa*s for a degree of viscosity.

Figure 12:
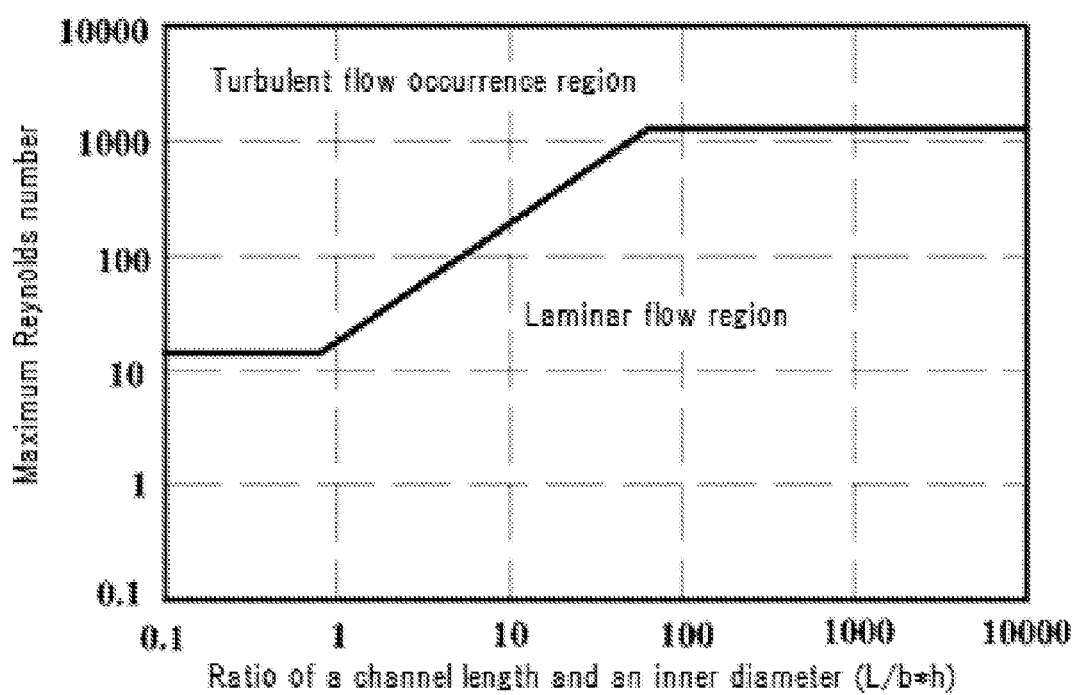
FIG. 12 is a graph for showing the relationship among the dimension of a flow passage, the maximum Reynolds number, a laminar flow region, and a turbulent flow region.
Figure 13:
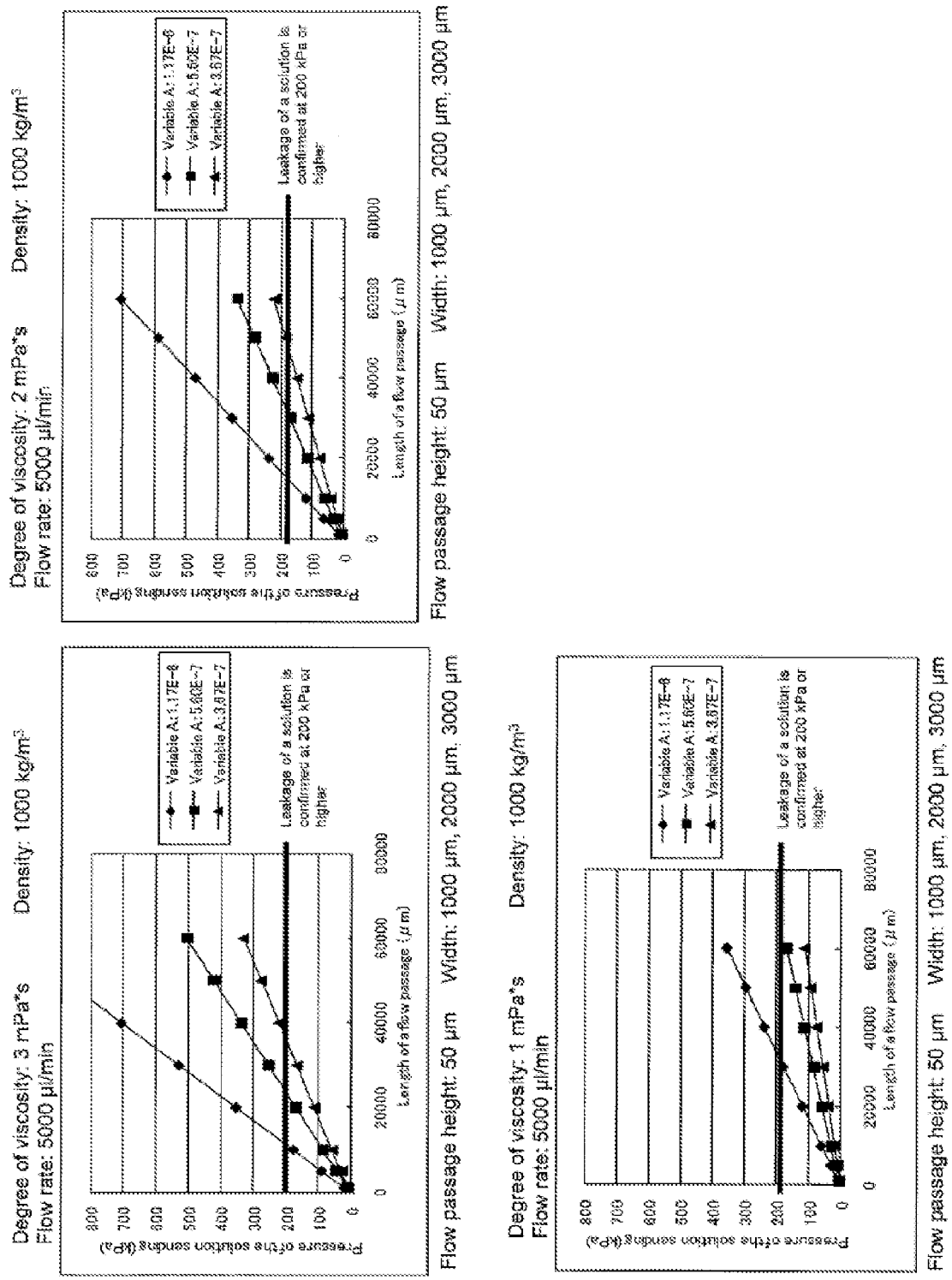
FIG. 13 is a graph for showing the relationship between a length of a flow passage and a pressure of the solution sending.
Figure 14:
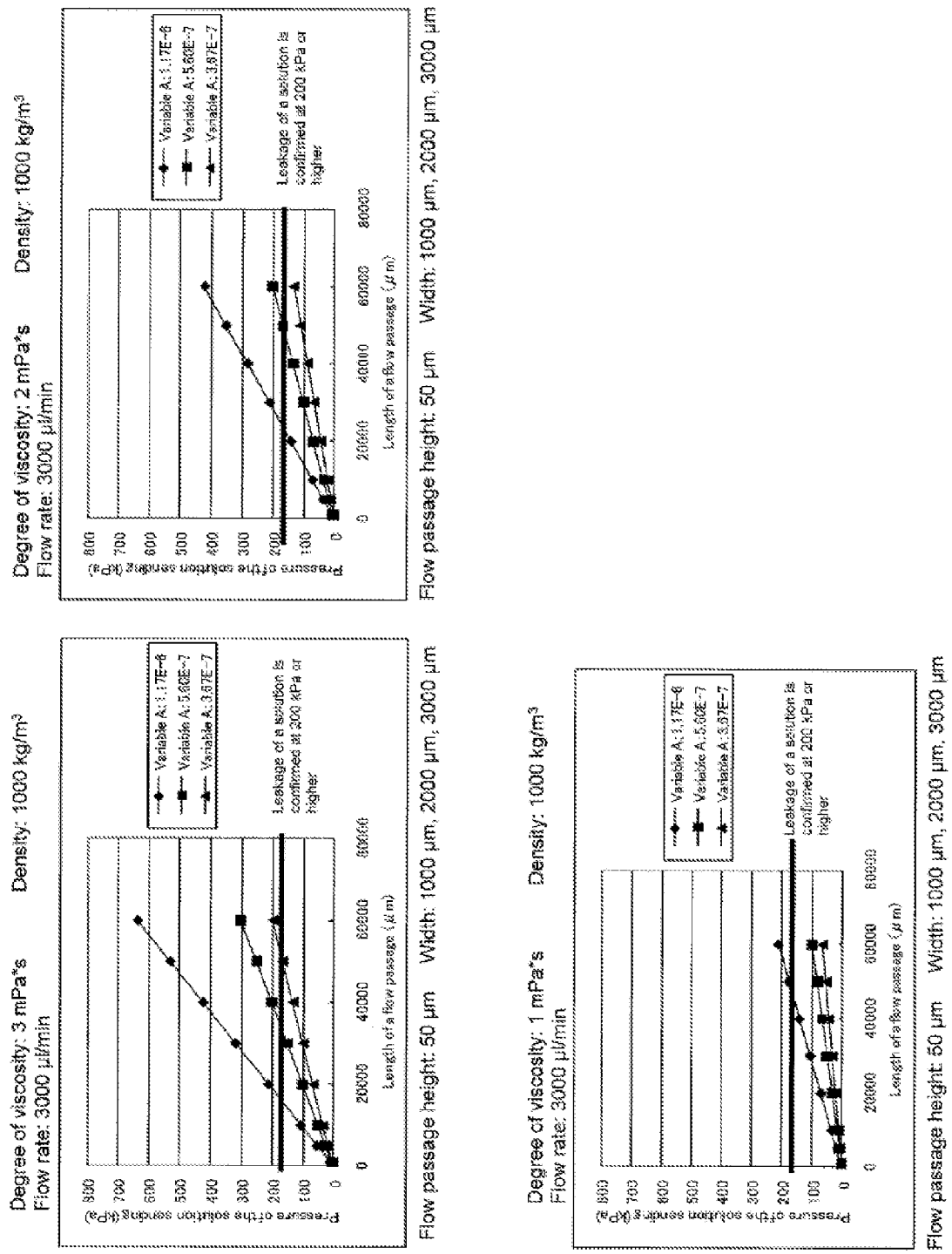
FIG. 14 is a graph for showing the relationship between a length of a flow passage and a pressure of the solution sending.
Figure 15:
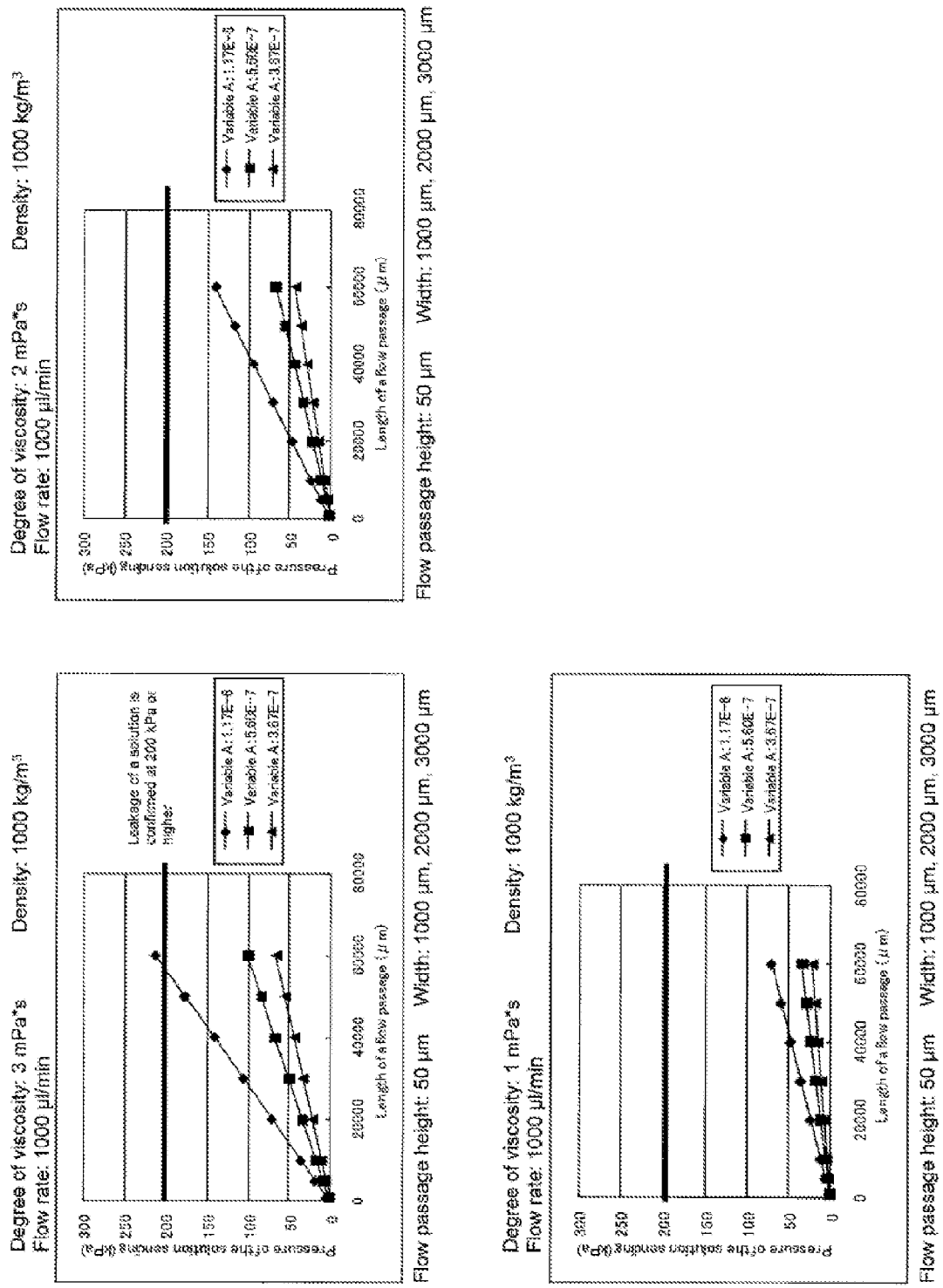
FIG. 15 is a graph for showing the relationship between a length of a flow passage and a pressure of the solution sending.
Figure 16:
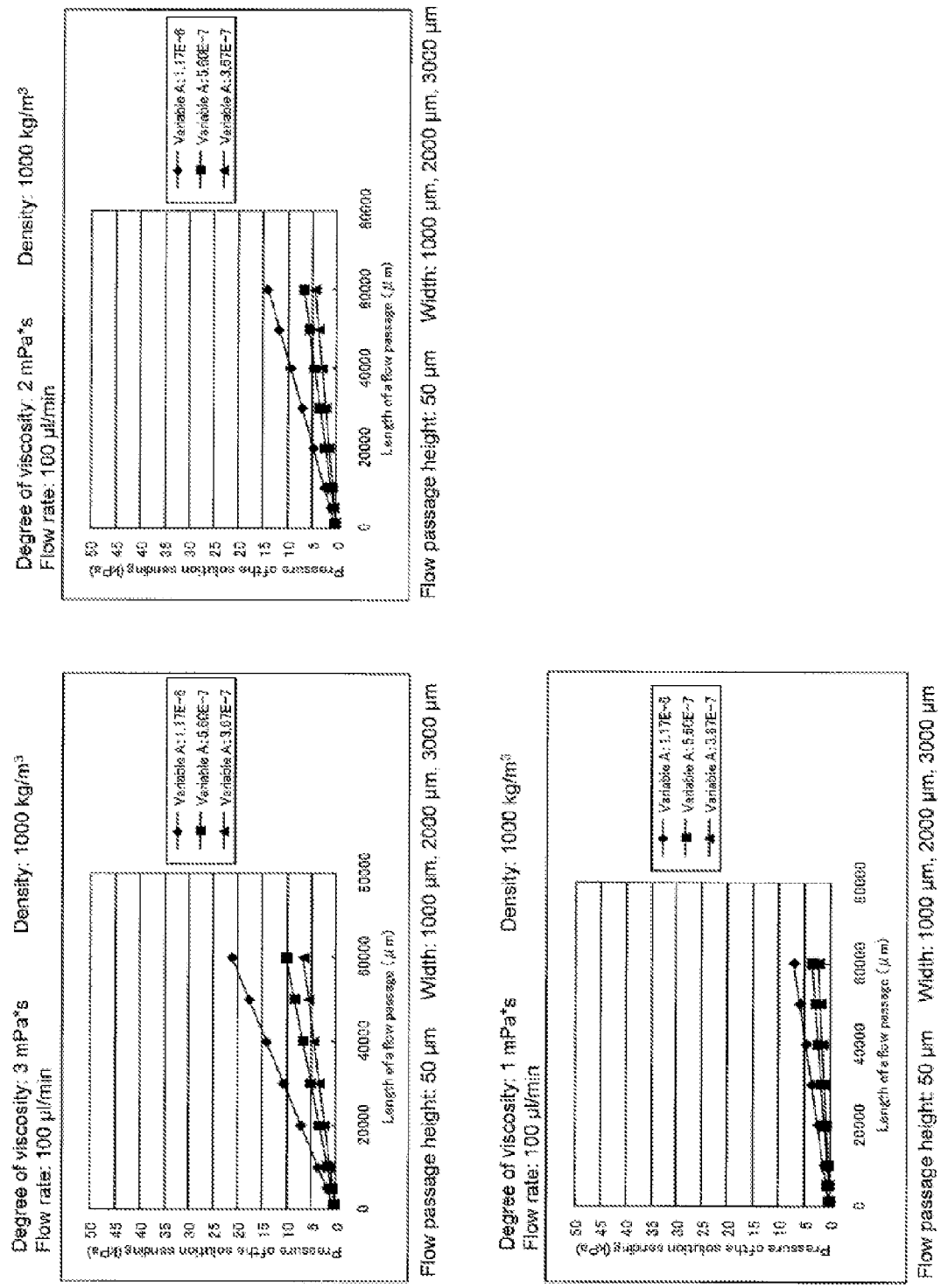
FIG. 16 is a graph for showing the relationship between a length of a flow passage and a pressure of the solution sending.

By this configuration, as shown in Table 2 that will be described later and FIG. 12, a solution that flows in the flow passage is in the range of a laminar flow region, a turbulent flow does not occur in the flow passage, and a laminar flow causes a uniform flow. Consequently, a stagnation of a solution does not occur in the flow passage. As a result, the detection region in the flow passage is not provided with a disturbance of the index of refraction, and a fluctuation of a signal can be prevented from occurring during a detection, whereby an inspection can be carried out in a precise manner.

More specifically for a pressure (kPa), as shown by the following expression, a pressure of the solution sending that is applied to a flow passage is decided depending on a degree of viscosity of a solution and a speed of the solution sending to a certain shape of a flow passage. In other words:

a pressure ((kPa))=(resistance of the flow passage)× (flow rate/60)

A resistance of the flow passage that occurs in the case in which a certain solution is made flow in a flow passage of a certain shape is represented by the following expression:

(resistance of the flow passage)=8×{(flow passage height h+flow passage width b)²/(flow passage height h×flow passage width b)³}×(viscosity)× (flow passage length L)×10³

That is to say, a pressure ((kPa))=8×{(flow passage height h+flow passage width b)²/(flow passage height h×flow passage width b)³}×(viscosity)×(flow passage length L)×10³×(flow rate/60)

Here, for the system, a solution in which a degree of viscosity at 20° C. is in the range of 1 to 3 mPa*s is sent at an average flow rate in the range of 1 to 5000 μl/min.

By the above configuration, it can be set that the variable $A=8\times[(\text{flow passage height h}+\text{flow passage width b})^2\times10^3/\{(\text{flow passage height h}\times\text{flow passage width b})^3\times60\}]$.

About the variable, for the system in which a solution in which a degree of viscosity at 20° C. is in the range of 1 to 3 mPa*s is sent at an average flow rate in the range of 1 to 5000 μl/min, an experiment has been carried out while the flow passage height h and the flow passage width b are varied (FIGS. 13 to 22). As a result, a leakage of a solution has been confirmed at 200 kPa or higher as shown by the graphs shown in FIGS. 13 to 15.

Consequently, it can be found that it is preferable to satisfy a flow passage length L×a variable A<200 (kPa).

Here, the units are μl/min for a flow rate, μm for a flow passage height, μm for a flow passage width, μm for a flow passage length, and mPa*s for a degree of viscosity.

In other words, for the system in which a solution in which a degree of viscosity at 20° C. is in the range of 1 to 3 mPa*s is sent at an average flow rate in the range of 1 to 5000 μl/min, in the case in which a numerical value that is obtained by multiplying a variable A by a flow passage length L exceeds 200 (kPa), an upper limit of a pressure resistance of a flow passage is exceeded. As a result, a leakage of a solution occurs, a solution sending cannot be carried out, and a correct measurement result cannot be obtained.

Figure 17:
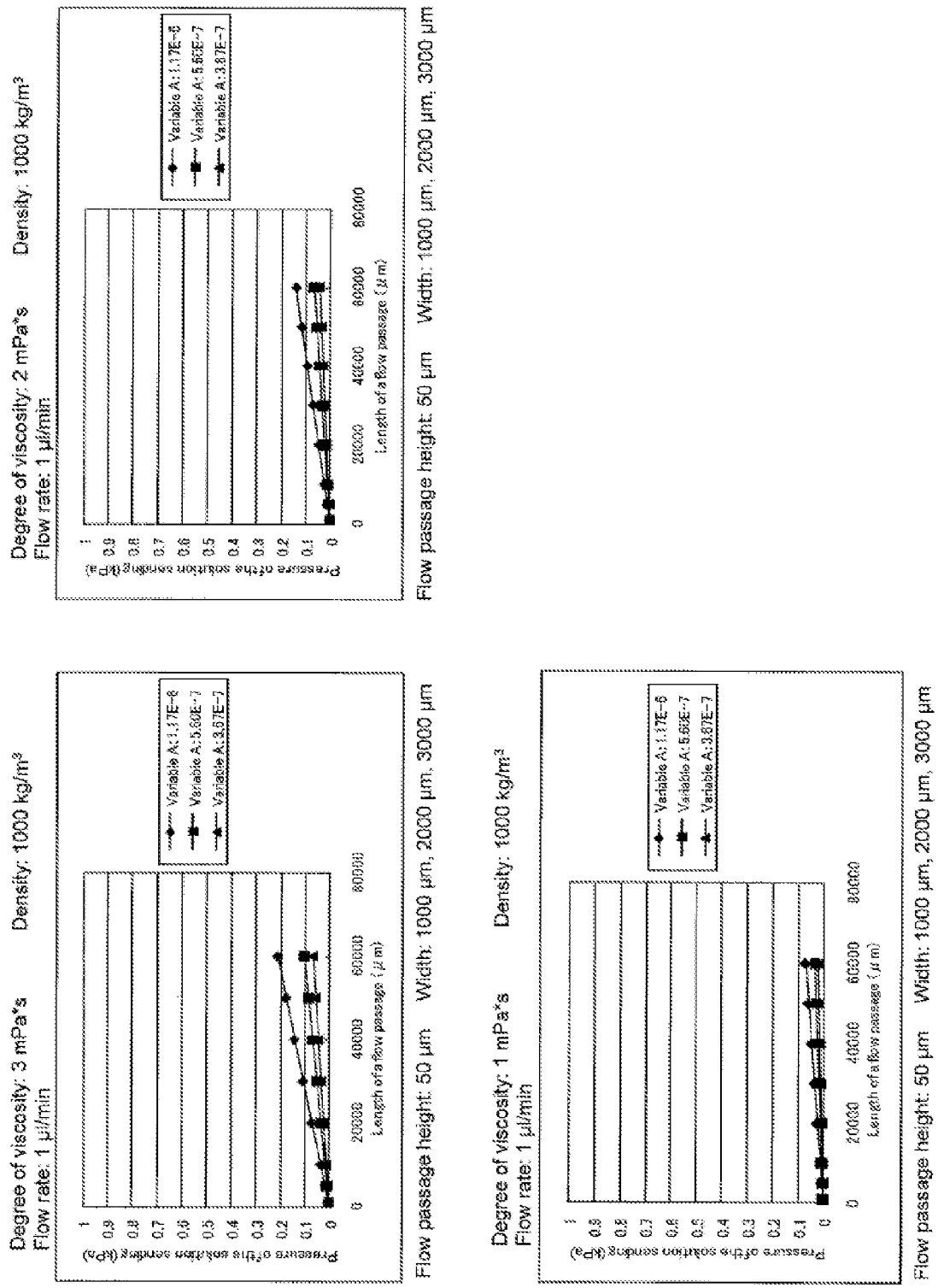
FIG. 17 is a graph for showing the relationship between a length of a flow passage and a pressure of the solution sending.
Figure 18:
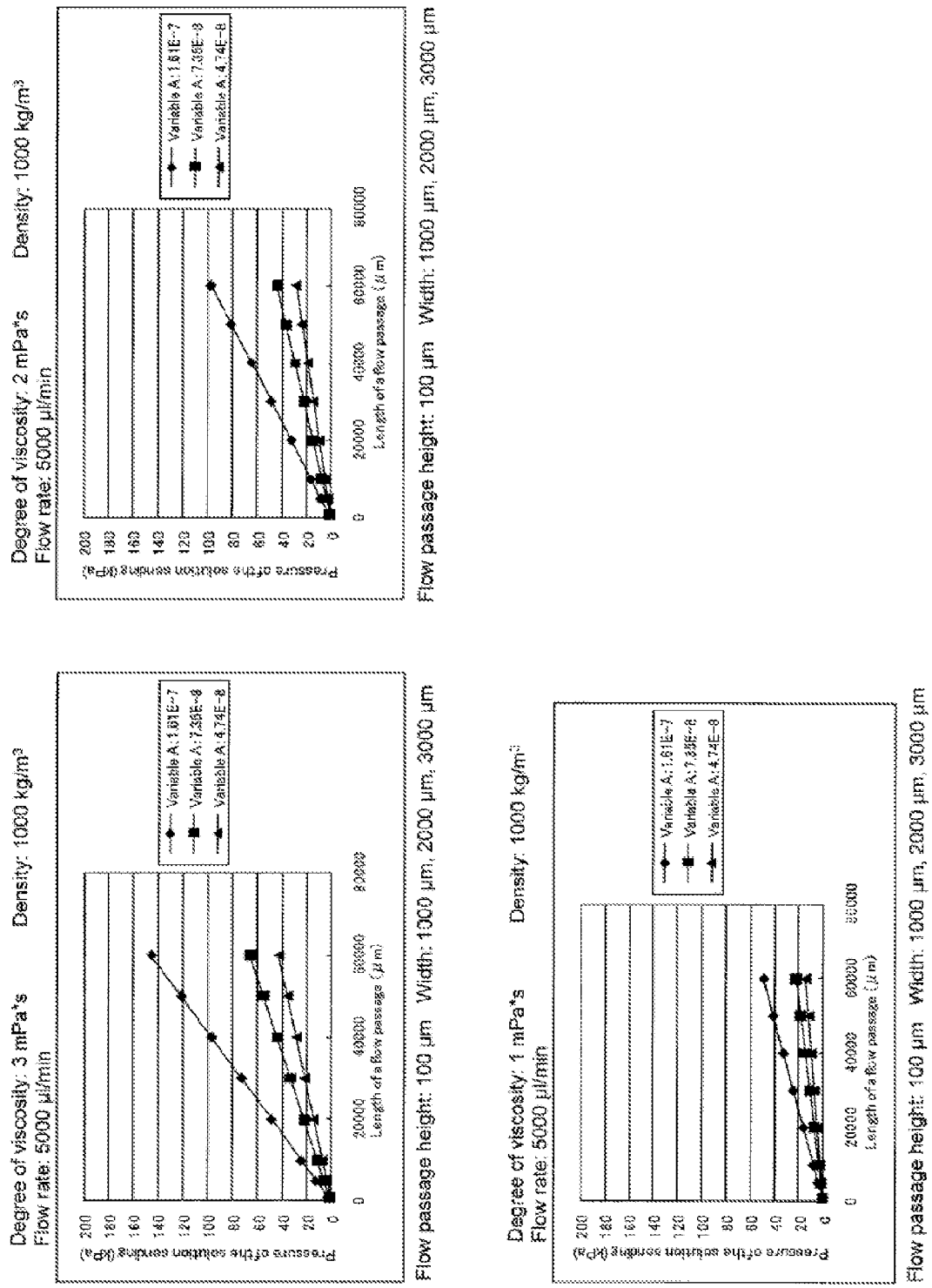
FIG. 18 is a graph for showing the relationship between a length of a flow passage and a pressure of the solution sending.
Figure 19:
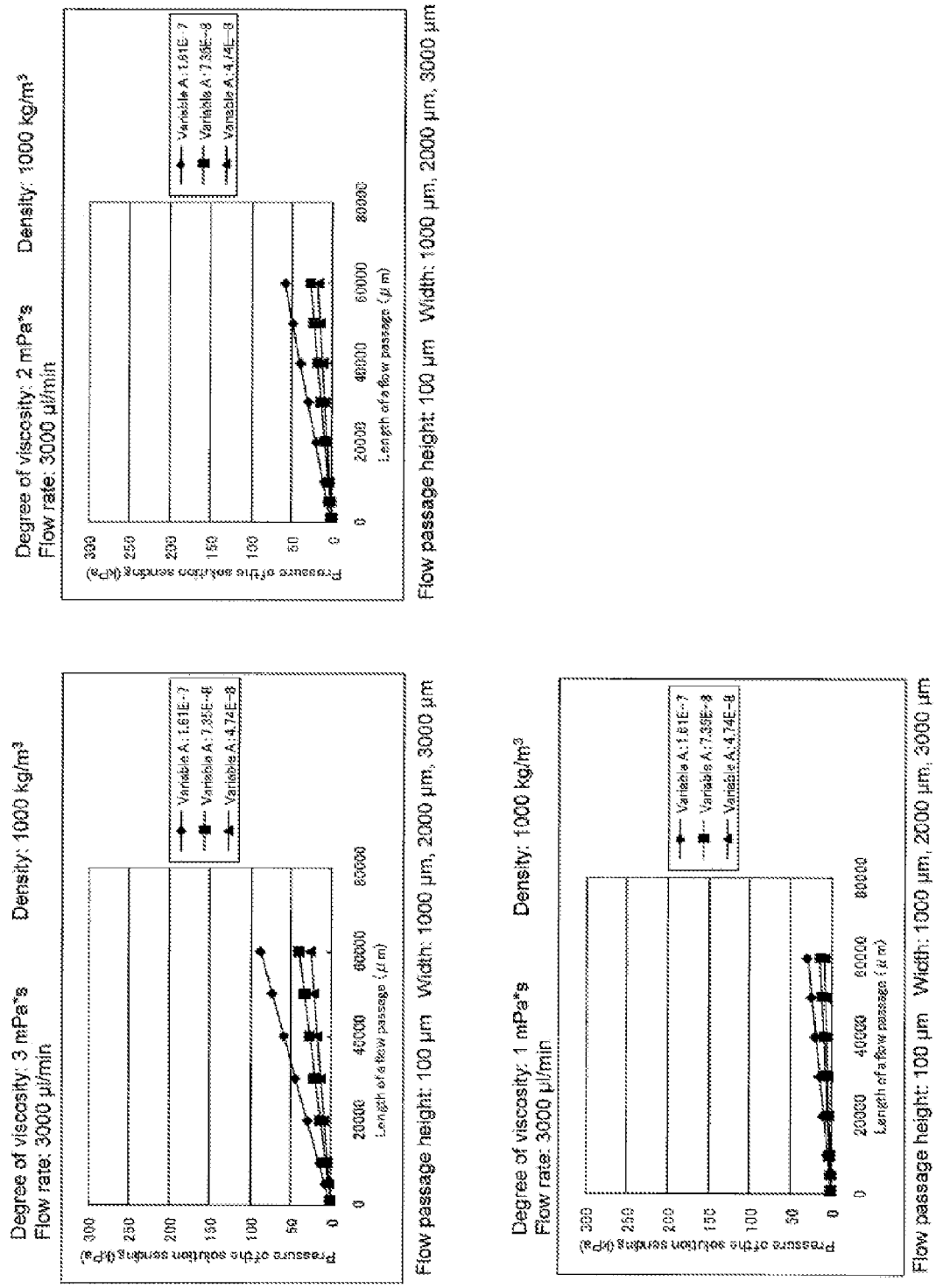
FIG. 19 is a graph for showing the relationship between a length of a flow passage and a pressure of the solution sending.
Figure 20:
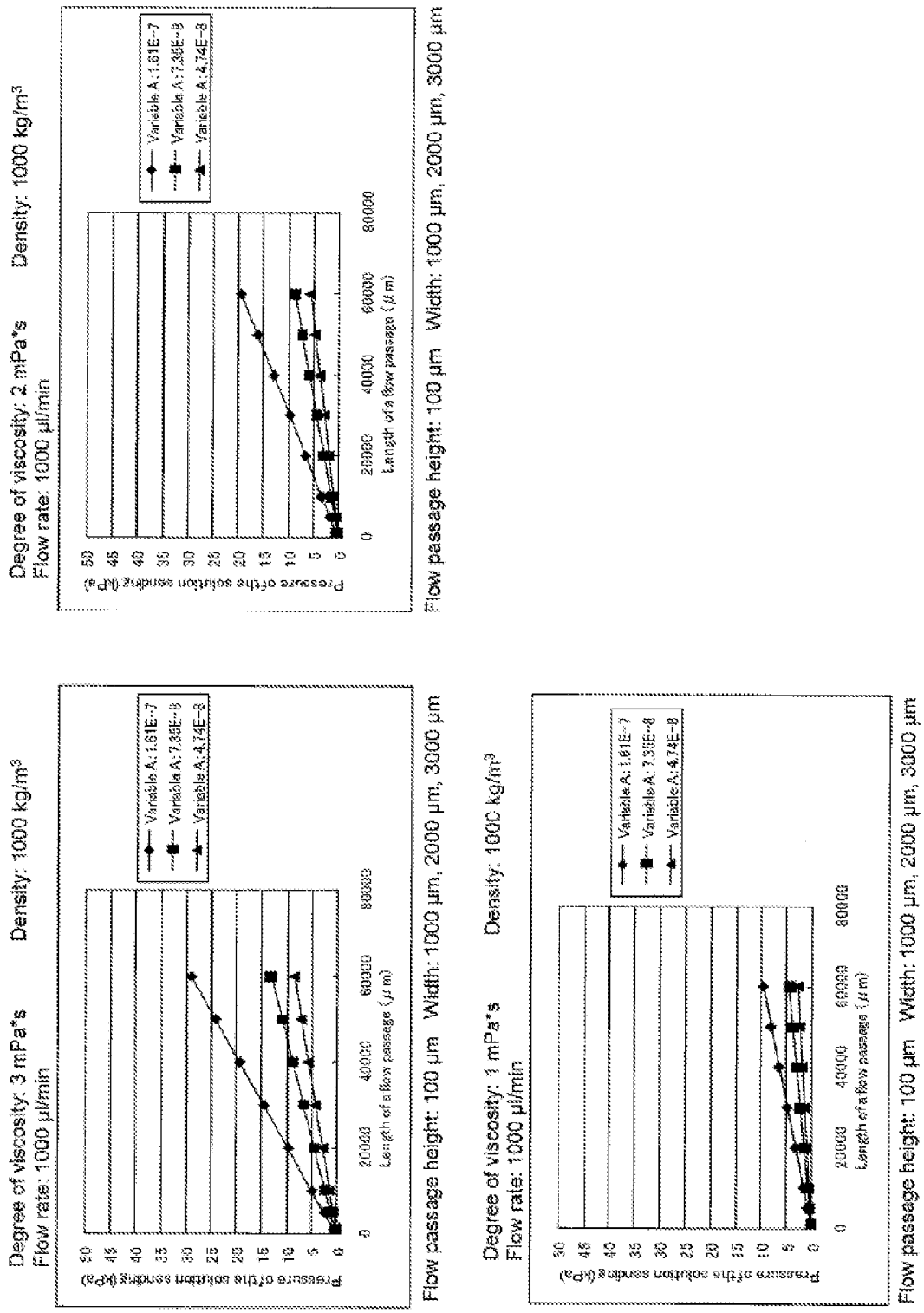
FIG. 20 is a graph for showing the relationship between a length of a flow passage and a pressure of the solution sending.
Figure 21:
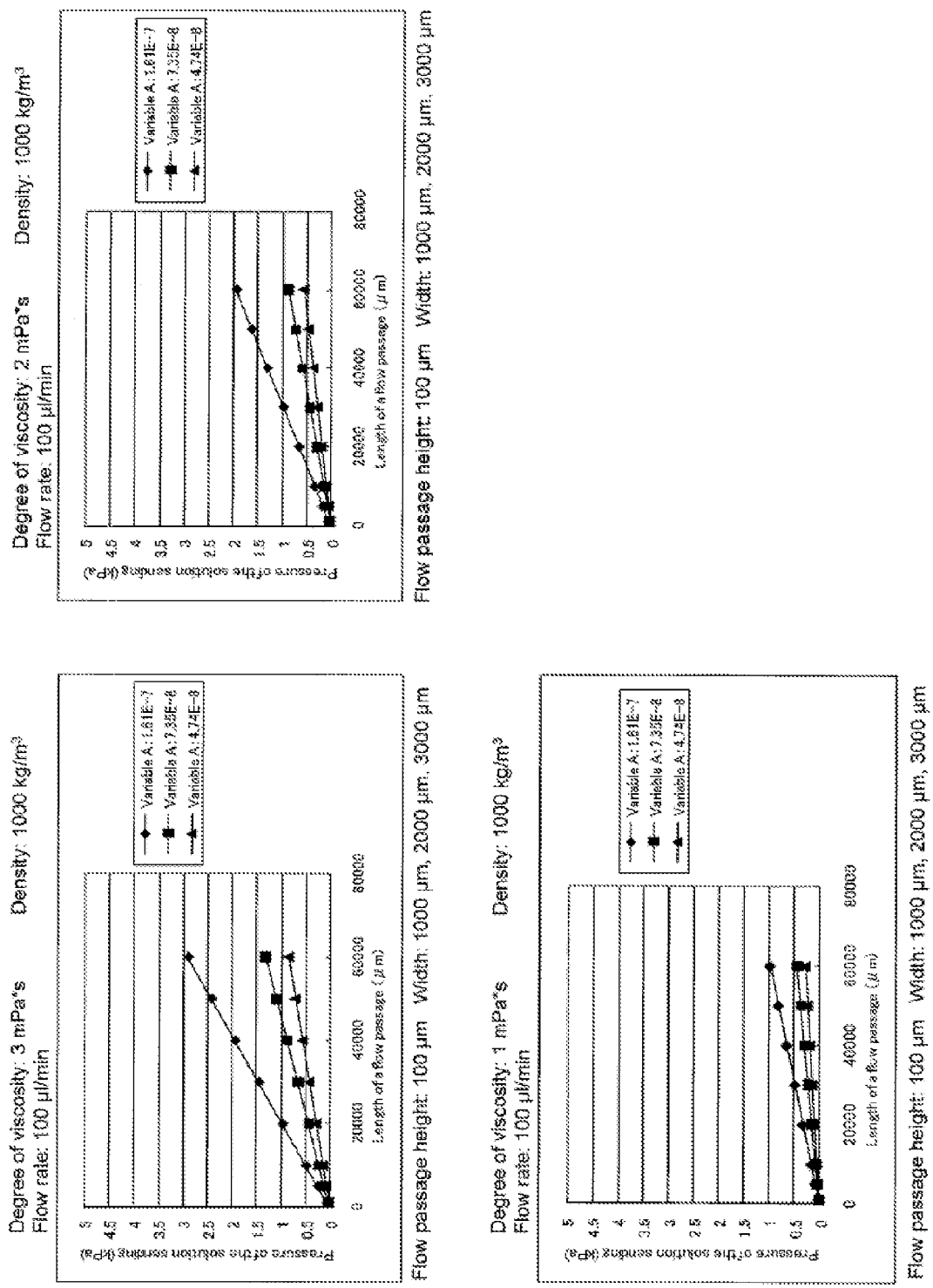
FIG. 21 is a graph for showing the relationship between a length of a flow passage and a pressure of the solution sending.

For the above experiment, in the case in which a density was 1000 kg/m³ and a flow passage height h was 50 μm, a degree of viscosity was varied among 1 mPa*s, 2 mPa*s, and 3 mPa*s, and a flow passage width b was varied among 1000 μm, 2000 μm, and 3000 μm, and a flow rate was varied among 5000 μl/min (FIG. 13), 3000 μl/min (FIG. 14), 1000 μl/min (FIG. 15), 100 μl/min (FIG. 16), and 1 μl/min (FIG. 17). FIGS. 13 to 17 show the results of the above experiment.

Figure 22:
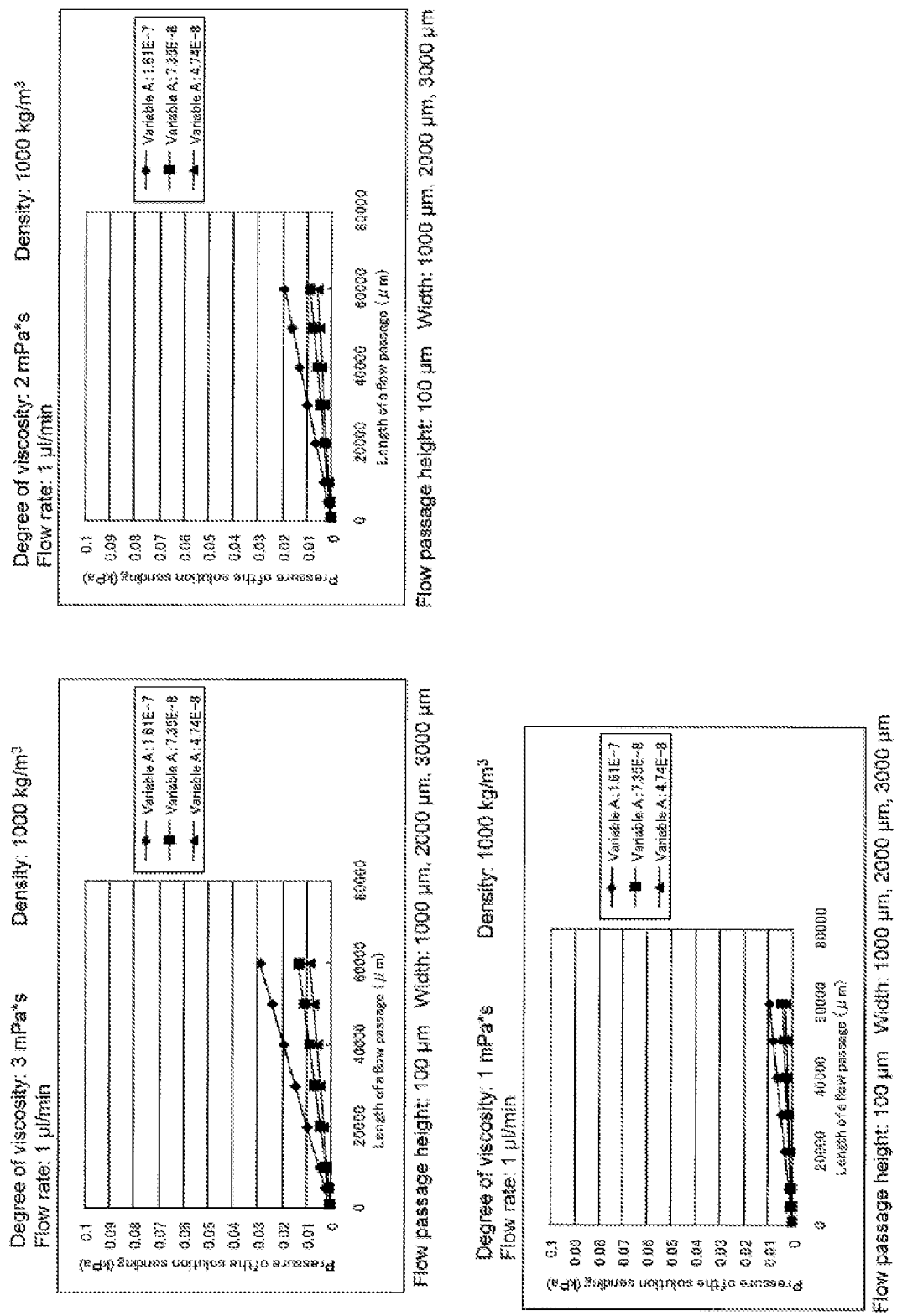
FIG. 22 is a graph for showing the relationship between a length of a flow passage and a pressure of the solution sending.
Figure 23:
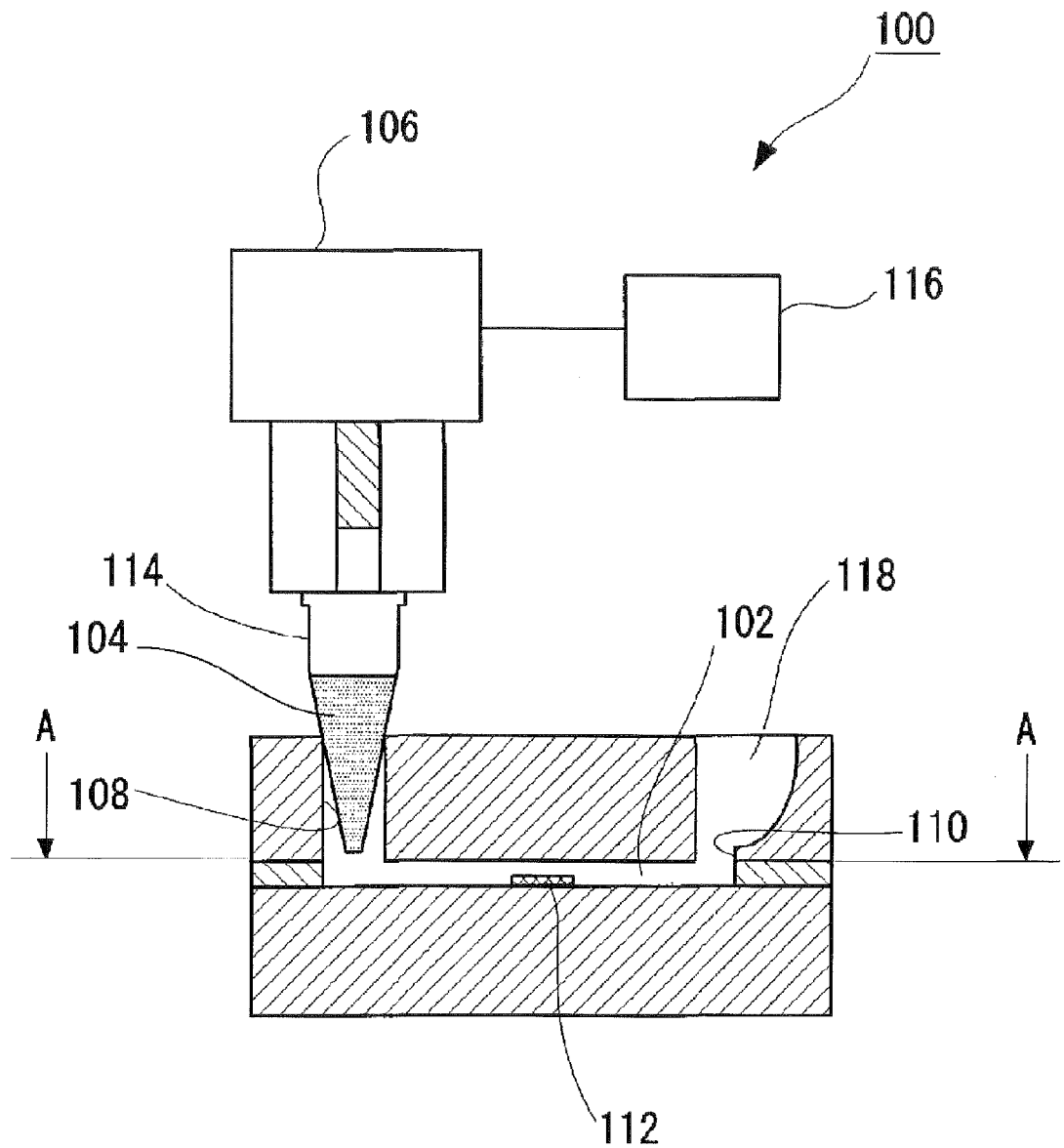
FIG. 23 is a cross sectional view for illustrating a conventional specimen material detection device.

For the above experiment, in the case in which a density was 1000 kg/m³ and a flow passage height h was 100 μm, a degree of viscosity was varied among 1 mPa*s, 2 mPa*s, and 3 mPa*s, and a flow passage width b was varied among 1000 μm, 2000 μm, and 3000 μm, and a flow rate was varied among 5000 μl/min (FIG. 18), 3000 μl/min (FIG. 19), 1000 μl/min (FIG. 20), 100 μl/min (FIG. 21), and 1 μl/min (FIG. 22). FIGS. 18 to 22 show the results of the above experiment.

TABLE 2

| Flow passage height h (mm) | IF diameter a (mm) | Flow passage width b (mm) | Flow rate (μl/min) | Reynolds number (Re) | Flow passage width L (mm) | L/b*h | Average value of a signal | Standard deviation | Variation coefficient CV |
|---|---|---|---|---|---|---|---|---|---|
| 0.1 | 3 | 1 | 3000 | 50.0 | 0.5 | 5 | 322333 | 21126.6 | 6.6 |
| 0.1 | 3 | 1 | 3000 | 50.0 | 1 | 10 | 325000 | 6244.98 | 1.9 |
| 0.1 | 3 | 1 | 3000 | 50.0 | 10 | 100 | 321667 | 5507.571 | 1.7 |
| 0.1 | 3 | 1 | 3000 | 50.0 | 50 | 500 | 324667 | 3214.55 | 1.0 |
| 0.1 | 3 | 1 | 5000 | 83.3 | 0.5 | 5 | 429000 | 22605.31 | 5.3 |
| 0.1 | 3 | 1 | 5000 | 83.3 | 1 | 10 | 428333 | 7637.626 | 1.8 |
| 0.1 | 3 | 1 | 5000 | 83.3 | 10 | 100 | 431667 | 9865.766 | 2.3 |

TABLE 2-continued

| Flow passage height h (mm) | IF diameter a (mm) | Flow passage width b (mm) | Flow rate (μl/min) | Reynolds number (Re) | Flow passage width L (mm) | L/b*h | Average value of a signal | Standard deviation | Variation coefficient CV |
|---|---|---|---|---|---|---|---|---|---|
| 0.1 | 3 | 1 | 5000 | 83.3 | 50 | 500 | 428667 | 7767.453 | 1.8 |
| 0.1 | 3 | 1 | 10000 | 166.7 | 0.5 | 5 | 438667 | 24583.19 | 5.6 |
| 0.1 | 3 | 1 | 10000 | 166.7 | 1 | 10 | 439333 | 5131.601 | 1.2 |
| 0.1 | 3 | 1 | 10000 | 166.7 | 10 | 100 | 441667 | 1527.525 | 0.3 |
| 0.1 | 3 | 1 | 10000 | 166.7 | 50 | 500 | 440667 | 5131.601 | 1.2 |
| 0.2 | 3 | 1 | 3000 | 50.0 | 0.5 | 2.5 | 289000 | 18734.99 | 6.5 |
| 0.2 | 3 | 1 | 3000 | 50.0 | 1 | 5 | 280667 | 3785.939 | 1.3 |
| 0.2 | 3 | 1 | 3000 | 50.0 | 10 | 50 | 276333 | 4509.25 | 1.6 |
| 0.2 | 3 | 1 | 3000 | 50.0 | 50 | 250 | 279667 | 1527.525 | 0.5 |
| 0.2 | 3 | 1 | 5000 | 83.3 | 0.5 | 2.5 | 325333 | 17502.38 | 5.4 |
| 0.2 | 3 | 1 | 5000 | 83.3 | 1 | 5 | 323667 | 3214.55 | 1.0 |
| 0.2 | 3 | 1 | 5000 | 83.3 | 10 | 50 | 326333 | 5131.601 | 1.6 |
| 0.2 | 3 | 1 | 5000 | 83.3 | 50 | 250 | 325333 | 3511.885 | 1.1 |

For Table 2, a solution that is provided with a density ρ of 1000 (kg/m$^3$) and a viscosity μ of 0.001 (kg/m*s) has been used.

Moreover, for the present invention, it is preferable that a distance L from an end part on a side of the flow passage of the first inflow outflow hole 6 to a center of the detection region 4 is set to be in the range of 1 to 50 mm.

In the case in which a distance L from an end part on a side of the flow passage of the first inflow outflow hole 6 to a center of the detection region 4 is set to be in the range of 1 to 50 mm as described above, a turbulent flow does not occur in the fine flow passage 2, and a laminar flow causes a uniform flow. Consequently, a stagnation of a solution 16 does not occur in the fine flow passage 2. As a result, the detection region in the fine flow passage 2 is not provided with a disturbance of the index of refraction, and a fluctuation of a signal can be prevented from occurring during a detection, whereby an inspection can be carried out in a precise manner.

As shown in Table 3, in the case in which a distance L from an end part on a side of the flow passage of the first inflow outflow hole 6 to a center of the detection region 4 exceeds 50 mm and becomes 60 mm, when a solution flows at a high flow rate such as a flow rate of 10000 μl/min, a pressure becomes large so as to be 96.8 kPa and a leakage of a solution has the potential to occur.

Although a pressure depends on a degree of viscosity of a solution, in the case in which a distance L is 60 mm and a degree of viscosity of a solution is larger than 0.001 kg/m*s, a pressure is further increased and a leakage of a solution has the higher potential to occur. Consequently, it is preferable that a distance L is set to be in the range of 1 to 50 mm.

TABLE 3

| Viscosity μ (kg/m*s) | Density ρ (kg/m$^3$) | Flow passage height h (mm) | Flow passage width b (mm) | Flow passage length L (mm) | Flow rate (μl/min) | Pressure (kPa) |
|---|---|---|---|---|---|---|
| 0.001 | 1000 | 0.1 | 1 | 40 | 3000 | 19.4 |
| 0.001 | 1000 | 0.1 | 1 | 40 | 5000 | 32.3 |
| 0.001 | 1000 | 0.1 | 1 | 40 | 1000 | 64.5 |
| 0.001 | 1000 | 0.1 | 1 | 50 | 3000 | 24.2 |
| 0.001 | 1000 | 0.1 | 1 | 50 | 5000 | 40.3 |
| 0.001 | 1000 | 0.1 | 1 | 50 | 10000 | 80.7 |
| 0.001 | 1000 | 0.1 | 1 | 60 | 3000 | 29.0 |
| 0.001 | 1000 | 0.1 | 1 | 60 | 5000 | 48.4 |
| 0.001 | 1000 | 0.1 | 1 | 60 | 10000 | 96.8 |

In the present embodiment, the descriptions have been made for the relationship between the maximum width (a) of the first inflow outflow hole 6 and the width (b) of the fine flow passage 2 and a distance L from an end part on a side of the flow passage of the first inflow outflow hole 6 to a center of the detection region 4. Moreover, it is preferable that the configuration similar to the above is set for the relationship between the maximum width (a) of the second inflow outflow hole 8 and the width (b) of the fine flow passage 2 and a distance L from an end part on a side of the flow passage of the second inflow outflow hole 8 to a center of the detection region 4.

In other words, it is preferable that:

the relationship between the maximum width (a) of the second inflow outflow hole 8 and the width (b) of the fine flow passage 2 is a>b, and an angle θ that is formed between a wall surface of the fine flow passage 2 and the tangent line of the second inflow outflow hole 8 at a contact point of the second inflow outflow hole 8 and the fine flow passage 2 is in the range of 90°≤θ≤135°.

In the case in which a distance from an end part on a side of the flow passage of the second inflow outflow hole 8 to a center of the detection region 4 is set as L and a height of the fine flow passage 2 is set as h, it is preferable that a value of L/b*h is set to be in the range of 10 to 500.

Moreover, it is preferable that a distance L from an end part on a side of the flow passage of the second inflow outflow hole 8 to a center of the detection region 4 is set to be in the range of 1 to 50 mm.

By this configuration, residue of a solution can be prevented at the both ends in a direction of a width near a contact point of the second inflow outflow hole 8 and the fine flow passage 2, and an irregularity can be prevented from occurring in a concentration and a fluctuation of a signal can be prevented from occurring during a detection, whereby an inspection can be carried out in a precise manner.

While the preferred embodiments in accordance with the present invention have been described above, the present invention is not restricted to the embodiments described above. While a specimen material detection device that is called the reciprocation type has been described as the specimen material detection device 10 in the above embodiments, the specimen material detection device 10 in accordance with the present invention is not restricted to the embodiments described above. The present invention can also be applied to any one of the specimen material detection devices of a one pass type not shown, a circulation type not shown, and a reciprocation type.

While an air (an air damper) 26 is used as a driving gas for the specimen material detection device 10 in accordance with the present embodiment, an inert gas such as nitrogen and argon can also be used as a driving gas.

An example of a flowing operation of the solution 16 for the specimen material detection device 10 has been described with reference to FIGS. 3 and 4 in the above embodiment. However, the above embodiment is just an example consistently. In the above embodiments for instance, an air liquid interface S in the pipette 22 is lowered close to the height of the upper face of the flow passage of the fine flow passage 2. However, a driving can also be carried out in such a manner that an air liquid interface S is moved to a place close to the detection region 4 although it is not shown. In other words, the various changes, modifications, and functional additions can be thus made without departing from the scope of the present invention.

INDUSTRIAL APPLICABILITY

The present invention can be applied to a sensor chip and a specimen material detection device using a sensor chip for a surface plasmon resonance device (hereafter referred to as an SPR device) using a phenomenon of a surface plasmon resonance (SPR: Surface Plasmon Resonance) and a surface plasmon-field enhanced fluorescence spectroscopy measurement device (hereafter referred to as an SPFS device) using a principle of a surface plasmon excitation enhanced fluorescence spectroscopy (SPFS: Surface Plasmon-field enhanced Fluorescence Spectroscopy) for the fields of a medical care and biotechnology for instance.

REFERENCE SIGNS LIST

1: Sensor chip
2: Fine flow passage
2a: Wall surface
3: Dielectric member
4: Detection region
6: First inflow outflow hole
8: Second inflow outflow hole
10: Specimen material detection device
12: Control part
14: Solution sending pump
16: Solution
18: Light detection means
20: Mixing part
22: Pipette
22a: Leading end
22b: Base end part
24: Plunger
26: Air
28: Junction part
100: Specimen material detection device
102: Fine flow passage
104: Solution
106: Solution sending pump
108: Inflow outflow hole
110: Outlet hole
112: Detection region
114: Pipette
116: Control part
118: Mixing part
120: Solution back end

The invention claimed is:

1. A sensor chip that is used in a specimen material detection device, comprising:
a flow passage that is provided with a detection region; and
an inflow outflow hole that is connected to an edge part of one side of the flow passage and that is configured to be able to make a solution inflow to and outflow from the flow passage, wherein:

after a first solution is made inflow from the inflow outflow hole and the first solution is removed from the flow passage, a second solution is made inflow into the flow passage from the inflow outflow hole, or after a first solution is made inflow into the flow passage from the inflow outflow hole, a second solution is made inflow into a flow passage from the inflow outflow hole via a driving gas, the sensor chip is configured in such a manner that the relationship between the maximum width (a) of the inflow outflow hole and the width (b) of the flow passage is a>b, and an angle θ that is formed between a wall surface of the flow passage and the tangent line of the inflow outflow hole at a contact point of the inflow outflow hole and the flow passage is in the range of 90°≤θ≤135°:

for a system in which a distance L from an end part on a side of the flow passage of the inflow outflow hole to a center of the detection region is at least 1 mm, and a solution in which a degree of viscosity at 20° C. is in the range of 1 to 3 mPa*s is sent at an average flow rate in the range of 1 to 5000 μl/min, flow passage length L×variable A<200 (kPa), where the variable A=8×[(flow passage height h+flow passage width b)2×103/{(flow passage height h×flow passage width b)3×60}], and the units are μl/min for a flow rate, μm for a flow passage height, μm for a flow passage width, μm for a flow passage length, and mPa*s for a degree of viscosity.

2. The sensor chip as defined in claim 1, wherein a distance L from an end part on a side of the flow passage of the inflow outflow hole to a center of the detection region is set to be in the range of 1 to 50 mm.

3. The sensor chip as defined in claim 1, wherein a solution that is made inflow into the flow passage is reciprocated and passes through the detection region.

4. The sensor chip as defined in claim 3, wherein:
a second inflow outflow hole is connected to the other end side of the flow passage,
the relationship between the maximum width (a) of the second inflow outflow hole and the width (b) of the flow passage is a>b, and
an angle θ that is formed between a wall surface of the flow passage and the tangent line of the second inflow outflow hole at a contact point of the second inflow outflow hole and the flow passage is in the range of 90°≤θ≤135°.

5. The sensor chip as defined in claim 4, wherein:
for a system in which a distance L from an end part on a side of the flow passage of the second inflow outflow hole to a center of the detection region is at least 1 mm for the second inflow outflow hole, and a solution in which a degree of viscosity at 20° C. is in the range of 1 to 3 mPa*s is sent at an average flow rate in the range of 1 to 5000 μl/min, flow passage length L×variable A<200 (kPa), where the variable A=8×[(flow passage height h+flow passage width b)²×10³/{(flow passage height h×flow passage width b)³×60}], and the units are μl/min for a flow rate, μm for a flow passage height, μm for a flow passage width, μm for a flow passage length, and mPa*s for a degree of viscosity.

6. The sensor chip as defined in claim 5, wherein a distance L from an end part on a side of the flow passage of the second inflow outflow hole to a center of the detection region is set to be in the range of 1 to 50 mm.

7. The sensor chip as defined in claim 4, further comprising a mixing part at the second inflow outflow hole in such a manner that the mixing part is configured to store a solution that has passed through the detection region of the flow passage on a temporary basis and to stir the solution that has been stored.

8. A specimen material detection device comprising a sensor chip as defined in claim 1.

9. The specimen material detection device as defined in claim 8, wherein the specimen material detection device is a surface plasmon resonance device (an SPR device) or a surface plasmon field enhanced fluorescence spectroscopic measurement device (an SPFS device).

10. A sensor chip that is used in a specimen material detection device, comprising:
- a flow passage that is provided with a detection region; and
- an inflow outflow hole that is connected to an edge part of one side of the flow passage and that is configured to be able to make a solution inflow to and outflow from the flow passage, wherein:
- after a first solution is made inflow from the inflow outflow hole and the first solution is removed from the flow passage, a second solution is made inflow into the flow passage from the inflow outflow hole, or after a first solution is made inflow into the flow passage from the inflow outflow hole, a second solution is made inflow into a flow passage from the inflow outflow hole via a driving gas,
- the sensor chip is configured in such a manner that the relationship between the maximum width (a) of the inflow outflow hole and the width (b) of the flow passage is a>b, and an angle θ that is formed between a wall surface of the flow passage and the tangent line of the inflow outflow hole at a contact point of the inflow outflow hole and the flow passage is in the range of $90°≤θ≤135°$;
- a solution that is made inflow into the flow passage is reciprocated and passes through the detection region;
- a second inflow outflow hole is connected to the other end side of the flow passage,
- the relationship between the maximum width (a) of the second inflow outflow hole and the width (b) of the flow passage is a>b,
- an angle θ that is formed between a wall surface of the flow passage and the tangent line of the second inflow outflow hole at a contact point of the second inflow outflow hole and the flow passage is in the range of $90°≤θ≤135°$;
- for a system in which a distance L from an end part on a side of the flow passage of the second inflow outflow hole to a center of the detection region is at least 1 mm for the second inflow outflow hole, and a solution in which a degree of viscosity at 20° C. is in the range of 1 to 3 mPa*s is sent at an average flow rate in the range of 1 to 5000 μl/min,
- flow passage length L×variable A<200 (kPa),
- where the variable A=8×[(flow passage height h+flow passage width b)2×103/{(flow passage height h×flow passage width b)3×60}], and the units are μl/min for a flow rate, μm for a flow passage height, μm for a flow passage width, μm for a flow passage length, and mPa*s for a degree of viscosity.

\* \* \* \* \*

UNITED STATES PATENT AND TRADEMARK OFFICE
CERTIFICATE OF CORRECTION

| | | |
|---|---|---|
| PATENT NO. | : 9,080,940 B2 | Page 1 of 1 |
| APPLICATION NO. | : 14/125899 | |
| DATED | : July 14, 2015 | |
| INVENTOR(S) | : Youichi Aoki | |

It is certified that error appears in the above-identified patent and that said Letters Patent is hereby corrected as shown below:

Title page, item 75, inventor's address should read as follows: Fuchu-shi (JP)

Signed and Sealed this
Fifteenth Day of December, 2015

Michelle K. Lee
*Director of the United States Patent and Trademark Office*